US011877727B2

(12) United States Patent
Hane

(10) Patent No.: US 11,877,727 B2
(45) Date of Patent: Jan. 23, 2024

(54) ENDOSCOPE SYSTEM, CONTROL DEVICE, AND METHOD FOR CALCULATING FORCE INFORMATION

(71) Applicant: OLYMPUS CORPORATION, Tokyo (JP)

(72) Inventor: Jun Hane, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 527 days.

(21) Appl. No.: 17/155,550

(22) Filed: Jan. 22, 2021

(65) Prior Publication Data

US 2021/0161368 A1    Jun. 3, 2021

Related U.S. Application Data

(63) Continuation of application No. PCT/JP2018/028919, filed on Aug. 1, 2018.

(51) Int. Cl.
*A61B 1/005* (2006.01)
*A61B 1/00* (2006.01)

(52) U.S. Cl.
CPC ........ *A61B 1/0057* (2013.01); *A61B 1/00158* (2013.01); *A61B 2562/0223* (2013.01)

(58) Field of Classification Search
CPC .............. A61B 1/0057; A61B 1/00158; A61B 2562/0223; A61B 90/361;
(Continued)

(56) References Cited

U.S. PATENT DOCUMENTS

| 8,725,233 B2 * | 5/2014 | Nagano ................ A61B 5/6885 600/587 |
| 2007/0151390 A1 | 7/2007 | Blumenkranz et al. |

(Continued)

FOREIGN PATENT DOCUMENTS

| JP | 06-154153 A | 6/1994 |
| JP | 2007-090098 A | 4/2007 |

(Continued)

OTHER PUBLICATIONS

International Search Report dated Sep. 25, 2018 received in PCT/JP2018/028919.

*Primary Examiner* — Anh Tuan T Nguyen
*Assistant Examiner* — Shankar Raj Ghimire
(74) *Attorney, Agent, or Firm* — Scully, Scott, Murphy & Presser, P.C.

(57) ABSTRACT

An endoscope system includes an insertion portion receiving a first force from an enteric canal and applying a second force, which is a reaction, to the enteric canal, a detection device detecting a position of the insertion portion, and a processor. The processor calculates a position of a point of application, a direction, and a magnitude of the first force, performs an arithmetic operation of a shape/position of the insertion portion based on an output from the detection device, determines a reaction position at which the second force is received, based on position information of the insertion portion and on position information of the point of application of the first force, sets two fixed points where the enteric canal is fixed, and calculates information of a third force and a fourth force directed toward the two fixed points from the reaction position with respect to the second force.

9 Claims, 18 Drawing Sheets

(58) Field of Classification Search
CPC .... A61B 2034/2051; A61B 2034/2061; A61B 1/0051; A61B 2090/065
See application file for complete search history.

(56) References Cited

U.S. PATENT DOCUMENTS

| | | | |
|---|---|---|---|
| 2010/0292566 A1* | 11/2010 | Nagano | A61B 17/12 600/587 |
| 2014/0230562 A1* | 8/2014 | Yamamoto | A61B 1/009 73/800 |
| 2017/0303769 A1* | 10/2017 | Ito | A61B 1/009 |
| 2018/0184884 A1* | 7/2018 | Nakamura | A61B 1/00004 |
| 2019/0335981 A1* | 11/2019 | Hane | A61B 1/0011 |
| 2020/0197097 A1* | 6/2020 | Govari | A61B 34/20 |
| 2021/0048355 A1* | 2/2021 | Hane | G01D 5/20 |
| 2021/0161368 A1* | 6/2021 | Hane | A61B 1/0051 |

FOREIGN PATENT DOCUMENTS

| | | |
|---|---|---|
| JP | 2009-522016 A | 6/2009 |
| JP | 2013-094337 A | 5/2013 |
| JP | 2015-043988 A | 3/2015 |
| JP | 2017-083351 A | 5/2017 |
| WO | 2017/009905 A1 | 1/2017 |

* cited by examiner

ENDOSCOPE SYSTEM, CONTROL DEVICE, AND METHOD FOR CALCULATING FORCE INFORMATION

CROSS REFERENCE TO RELATED APPLICATION

This application is a continuation application of PCT/JP2018/028919 filed on Aug. 1, 2018, the entire contents of which are incorporated herein by this reference.

BACKGROUND OF THE INVENTION

1. Field of the Invention

The present invention relates to an endoscope system, a control device, and a method for calculating force information, and more particularly to an endoscope system including an endoscope to be inserted into an enteric canal of a subject, to a control device that allows connection of the endoscope, and to a method for calculating force information used at the time of inserting the endoscope into the enteric canal of the subject.

2. Description of the Related Art

An endoscope system including an endoscope, an image processing device and the like is widely used in the medical field, the industrial field, and other fields, the endoscope picking up images of an object inside a subject, the image processing device generating an observation image of the object being picked up by the endoscope.

When a flexible member, such as an insertion portion of an endoscope, or an arm of a medical or industrial small-diameter manipulator is inserted into the subject, the flexible member may come into contact with the subject, thus pressing the subject. Conventionally, it is known that information on an external force applied to the flexible member is calculated to estimate the effect on the subject caused by such pressing.

For example, Japanese Patent Application Laid-Open Publication No. 2009-522016 discloses a technique where a strain gauge is provided in an insertion portion of an endoscope to measure, by the strain gauge, the amount of force which the insertion portion receives from the subject when the insertion portion comes into contact with the surface of the subject.

Japanese Patent Application Laid-Open Publication No. 6-154153 discloses a detection device that detects the amount of force received from the organ inside the body cavity by using a pressure sensitive sensor provided in a distal end of an insertion portion of an endoscope.

Japanese Patent Application Laid-Open Publication No. 2013-094337 discloses a technique where a plurality of bending sensors are disposed at a tubular insertion portion in a distributed manner, and the arithmetic operation of operation support information is performed by performing combination arithmetic operation of detection information from the plurality of bending sensors, the operation support information including external force information relating to an external force applied at least to the tubular insertion portion.

SUMMARY OF THE INVENTION

One aspect of the present invention is directed to an endoscope system including: an insertion portion having a distal end and a proximal end, and inserted into an enteric canal of a subject from a side of the distal end of the insertion portion and coming into contact with an inner wall of the enteric canal, thus receiving a first force from the enteric canal, and applying a second force as a reaction force of the first force to the enteric canal, the insertion portion having flexibility; an insertion portion position detection device configured to detect a relative position of the insertion portion, inserted into the enteric canal, with respect to the enteric canal, and to output a detection signal; and a processor, wherein the processor is configured to calculate first force information including a position of a point of application of the first force in the insertion portion, a direction of the first force, and a magnitude of the first force, perform an arithmetic operation of shape information and position information of the insertion portion in the enteric canal based on the detection signal relating to a position of the insertion portion detected by the insertion portion position detection device, determine second force information including a reaction position, the reaction position being a position at which the enteric canal receives the second force, based on the position information of the insertion portion in the enteric canal obtained by the arithmetic operation, and on the position information, which is calculated, of the point of application of the first force in the insertion portion, set position information of a first fixed point and a second fixed point as a calculation condition, the first fixed point and the second fixed point being portions of the enteric canal that are partially fixed from outside the enteric canal, and calculate, based on the calculation condition which is set, third force/fourth force information such that a resultant force of a third force directed toward the first fixed point from the reaction position and a fourth force directed toward the second fixed point from the reaction position is balanced with the second force, the third force/fourth force information including a magnitude and a direction of the third force, and a magnitude and a direction of the fourth force.

One aspect of the present invention is directed to a control device connected to an endoscope including an insertion portion having a distal end and a proximal end, and inserted into an enteric canal of a subject from a side of the distal end of the insertion portion and coming into contact with an inner wall of the enteric canal, thus receiving a first force from the enteric canal, and applying a second force as a reaction force of the first force to the enteric canal, the insertion portion having flexibility, the control device including: an insertion portion position detection device configured to detect a relative position of the insertion portion, inserted into the enteric canal, with respect to the enteric canal, and to output a detection signal; and a processor, wherein the processor is configured to calculate first force information including a position of a point of application of the first force in the insertion portion, a direction of the first force, and a magnitude of the first force, perform an arithmetic operation of shape information and position information of the insertion portion in the enteric canal based on the detection signal relating to a position of the insertion portion detected by the insertion portion position detection device, determine second force information including a reaction position, the reaction position being a position at which the enteric canal receives the second force, based on the position information of the insertion portion in the enteric canal obtained by the arithmetic operation, and on the position information, which is calculated, of the point of application of the first force in the insertion portion, set position information of a first fixed point and a second fixed point as a calculation condition, the first fixed point and the second fixed point being portions of the enteric canal that are partially fixed from outside the enteric canal, and calculate, based on the calculation condition which is set, third force/fourth force information such that a resultant force of a third force directed toward the first fixed point from the reaction position and a fourth force directed toward the second fixed point from the reaction position is balanced with the second force, the third force/fourth force information including a magnitude and a direction of the third force, and a magnitude and a direction of the fourth force.

One aspect of the present invention is directed to a method for calculating force information, the method including: detecting a relative position of an insertion portion with respect to an enteric canal, and outputting a detection signal, the insertion portion having a distal end and a proximal end, and being inserted into the enteric canal of a subject from a side of the distal end of the insertion portion and coming into contact with an inner wall of the enteric canal, thus receiving a first force from the enteric canal, and applying a second force as a reaction force of the first force to the enteric canal, the insertion portion having flexibility; calculating first force information including a position of a point of application of the first force in the insertion portion inserted into the enteric canal, a direction of the first force, and a magnitude of the first force; performing an arithmetic operation of shape information and position information of the insertion portion in the enteric canal based on the detection signal relating to a position of the insertion portion detected; determining second force information including a reaction position, the reaction position being a position at which the enteric canal receives the second force, based on the position information of the insertion portion in the enteric canal obtained by the arithmetic operation, and on the position information, which is calculated, of the point of application of the first force in the insertion portion; setting position information of a first fixed point and a second fixed point as a calculation condition, the first fixed point and the second fixed point being portions of the enteric canal that are partially fixed from outside the enteric canal; and calculating, based on the calculation condition which is set, third force/fourth force information such that a resultant force of a third force directed toward the first fixed point from the reaction position and a fourth force directed toward the second fixed point from the reaction position is balanced with the second force, the third force/fourth force information including a magnitude and a direction of the third force, and a magnitude and a direction of the fourth force.

DETAILED DESCRIPTION OF THE PREFERRED EMBODIMENTS

Hereinafter, embodiments of the present invention will be described with reference to drawings.

First Embodiment

Figure 1:
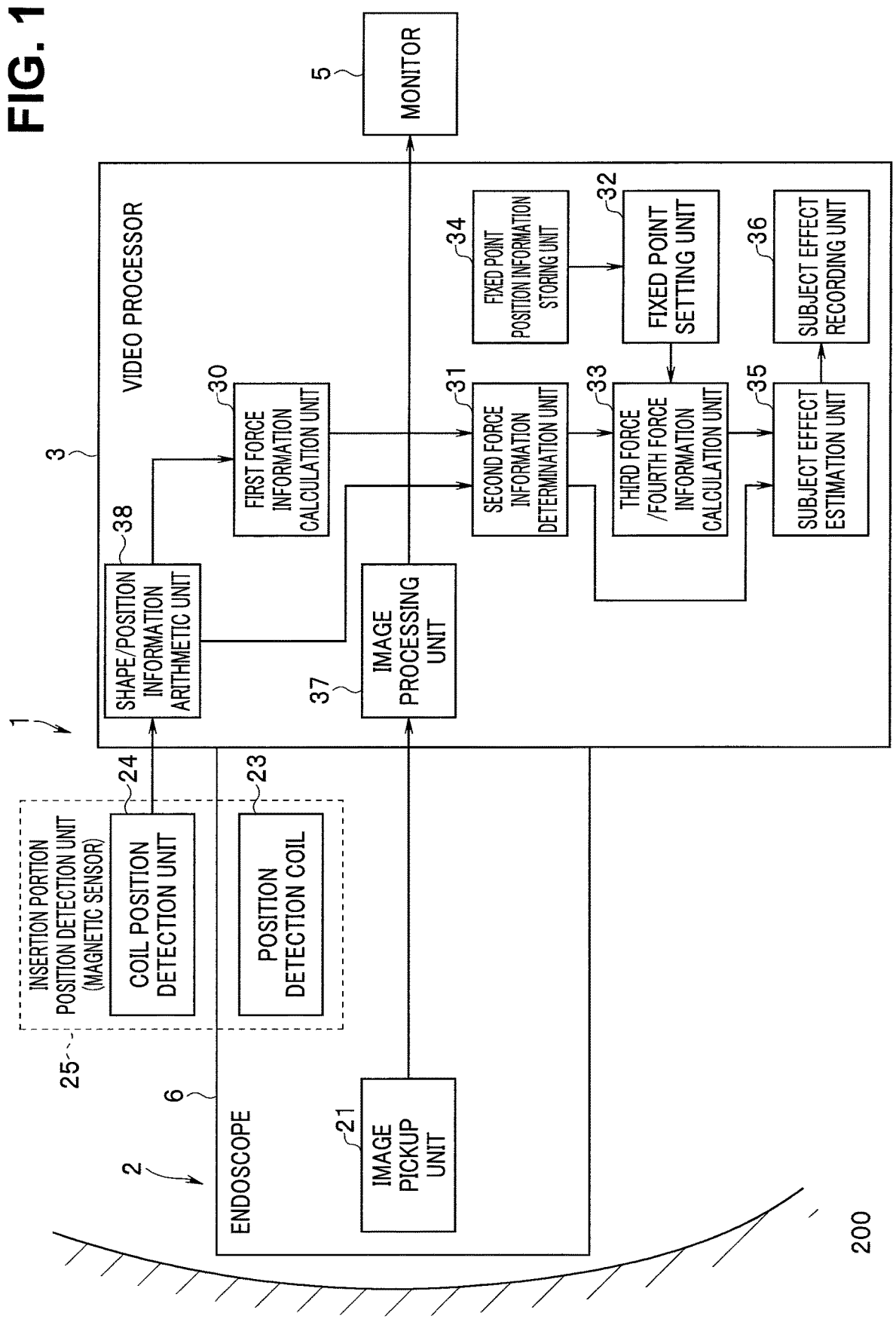
FIG. 1 is a block diagram showing a configuration of an endoscope system according to a first embodiment of the present invention.
Figure 2:
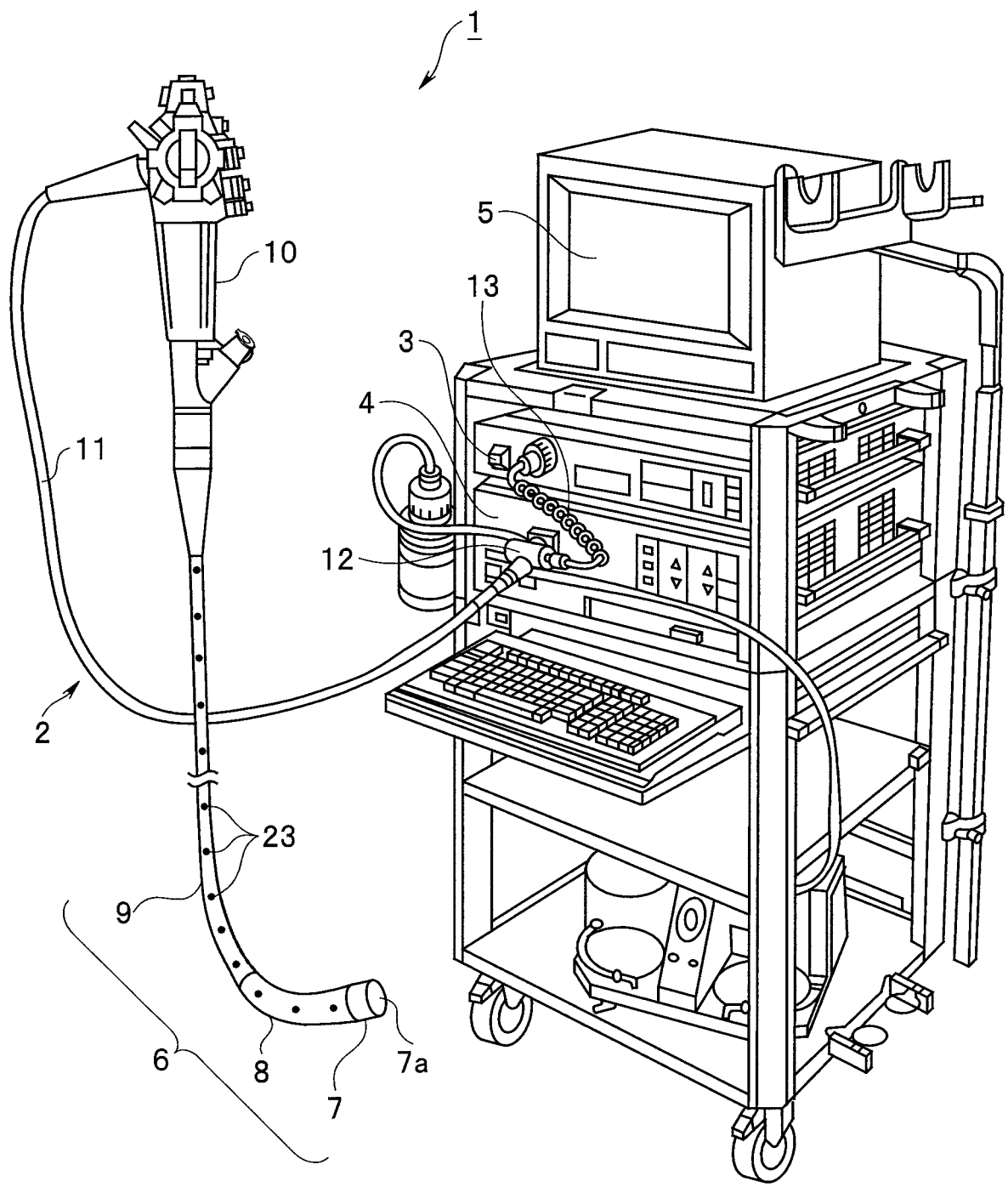
FIG. 2 is an external appearance view showing the configuration of the endoscope system of the first embodiment.

FIG. 1 is a block diagram showing a configuration of an endoscope system according to a first embodiment of the present invention. FIG. 2 is an external appearance view showing the configuration of the endoscope system of the first embodiment.

It is assumed that an endoscope system 1 of the first embodiment is an endoscope system including a so-called large intestine endoscope that is to be inserted into the enteric canal of a subject. It is known that the large intestine is an organ which varies in shape, arrangement or the like from person to person and which may particularly change shape due to the lapse of time, the insertion of an instrument or the like. It is also known that the large intestine includes the movable enteric canal and the fixed enteric canal. The sigmoid colon and the transverse colon are classified as the movable enteric canal, which can freely move. The rectum (the upper rectum, the lower rectum), the anal canal, the descending colon, and the ascending colon are classified as the fixed enteric canal.

As shown in FIG. 1 and FIG. 2, the endoscope system 1 according to the first embodiment includes an endoscope (large intestine endoscope) 2, a video processor 3, a light source device 4, and a monitor 5. The endoscope 2 allows observation and image pick-up of the enteric canal of a subject 200. The video processor 3 is connected to the endoscope 2 to receive the input of an image pickup signal and to perform predetermined image processing, and acts as a control device. The light source device 4 supplies illumination light for illuminating the subject. The monitor 5 displays an observation image corresponding to the image pickup signal.

<Configuration of Endoscope 2>

As shown in FIG. 2, the endoscope 2 includes an elongated insertion portion 6, an endoscope operation portion 10, and a universal cord 11. The insertion portion 6 is to be inserted into the body cavity (the large intestine) of the subject. The endoscope operation portion 10 is provided close to a proximal end of the insertion portion 6, and is held by an operator in order to operate the endoscope 2. The universal cord 11 has one end portion extending from the side portion of the endoscope operation portion 10.

The insertion portion 6 includes a rigid distal end portion 7, a bendable bending portion 8, and a long flexible tube portion 9. The distal end portion 7 is provided close to a distal end of the insertion portion 6. The bending portion 8 is provided at a rear end of the distal end portion 7. The flexible tube portion 9 is provided at a rear end of the bending portion 8, and has flexibility. In the drawing, a distal end surface of the distal end portion 7 is indicated by reference character "7a".

The insertion portion 6 is inserted into the enteric canal of the subject from a distal end side of the insertion portion 6, and comes into contact with an inner wall of the enteric canal, thus receiving a pressing force (first force) from the enteric canal, and applying a second force, which is the reaction force of the first force, to the enteric canal. The first force and the second force will be described later in detail.

Returning to FIG. 2, a connector portion 12 is provided at a proximal end of the universal cord 11, and the connector portion 12 is connected to the light source device 4. In other words, a pipe sleeve (not shown in the drawing) protruding from a distal end of the connector portion 12 to form a connection end portion of a fluid pipeline and a light guide pipe sleeve (not shown in the drawing) forming an end portion for supplying illumination light are detachably connected to the light source device 4.

Further, one end of a connection cable 13 is connected to an electrical contact portion provided on a side surface of the connector portion 12. The connection cable 13 is internally provided with, for example, a signal line, a control signal line, and a power line, the signal line being provided for transmitting an image pickup signal from a solid-state image pickup device 21 (hereinafter also referred to as "image pickup unit 21") of the endoscope 2, the control signal line and the power line being provided for driving the solid-state image pickup device 21. Further, a connector portion at the other end of the connection cable 13 is connected to the video processor 3.

<Insertion Portion Position Detection Unit (Magnetic Sensor) 25>

In the first embodiment, a plurality of position detection coils 23 are arranged in the insertion portion 6 of the endoscope 2 ranging from the distal end portion 7 to the flexible tube portion 9, the plurality of position detection coils 23 forming an insertion portion position detection unit (insertion portion position detection device). Further, in the first embodiment, a coil position detection unit 24 (coil position detector) is, as shown in FIG. 1, provided in the vicinity of the insertion portion 6 internally provided with the position detection coils 23. For example, the coil position detection unit 24 is disposed in a state of being directly attached to the subject 200, or is disposed in a room where the endoscope system 1 is installed.

In the first embodiment, the position detection coils 23 and the coil position detection unit 24 form a magnetic sensor, thus acting as an insertion portion position detection unit 25 that detects the relative position of the insertion portion 6, inserted into the enteric canal of the subject 200, with respect to the enteric canal.

Hereinafter, the insertion portion position detection unit (magnetic sensor) 25 of the first embodiment will be described in detail.

Figure 3:
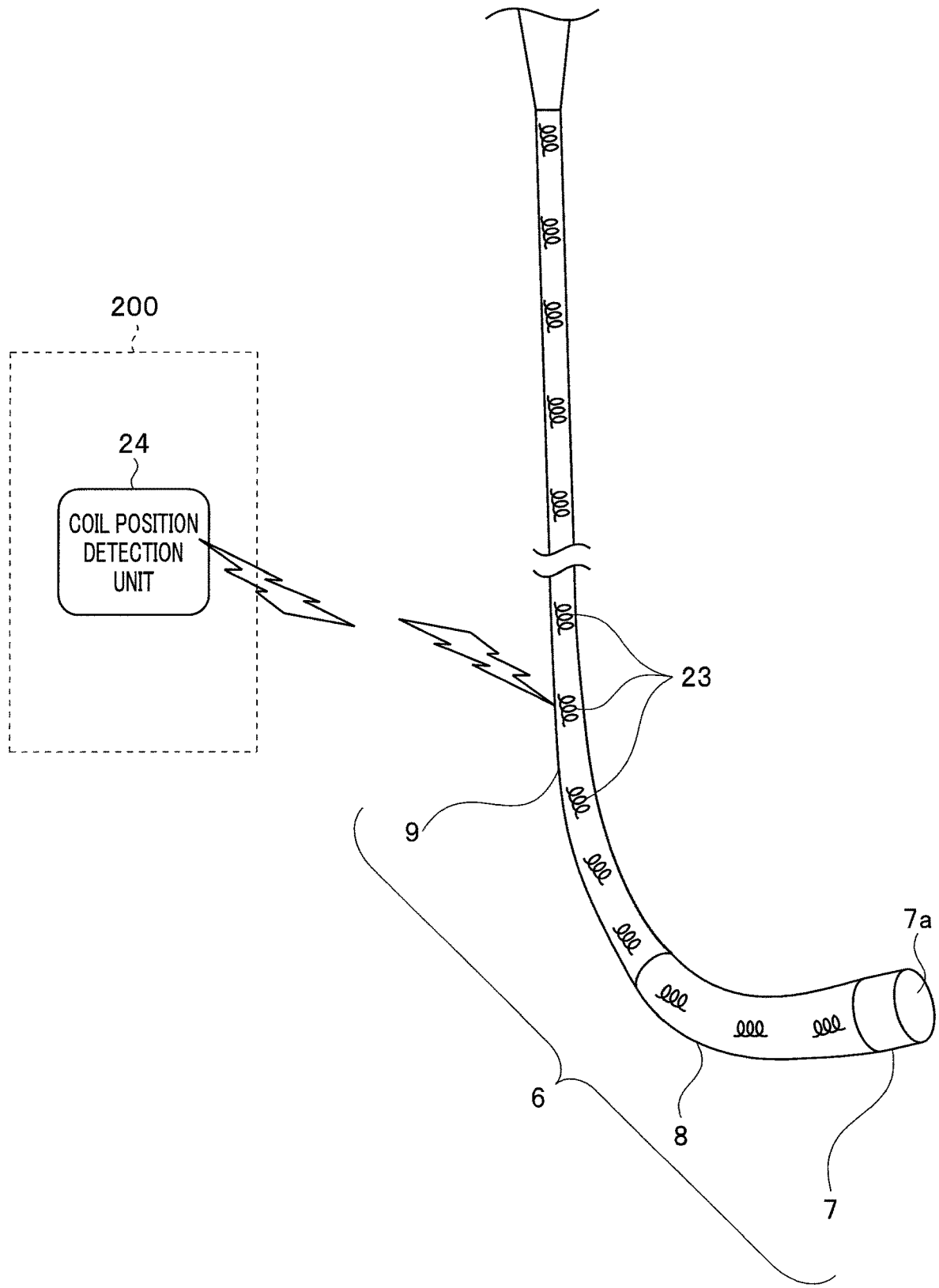
FIG. 3 is a view showing a configuration of an insertion portion position detection unit (magnetic sensor) of the endoscope system of the first embodiment.

FIG. 3 is a view showing a configuration of the insertion portion position detection unit (magnetic sensor) 25 of the endoscope system 1 of the first embodiment.

As described above, the insertion portion position detection unit (magnetic sensor) 25 is a sensor that detects a position of the insertion portion 6 inserted into the enteric canal of the subject 200. The position detection coils 23 are configured of a plurality of magnetic coils, and are arranged at intervals in a longitudinal direction of the insertion portion 6. The position detection coils 23 (magnetic coils) are driven by a drive unit not shown in the drawing to generate a predetermined magnetic field.

The coil position detection unit 24 having the function as a magnetic antenna is provided in the vicinity of the insertion portion 6 internally provided with the position detection coils 23. For example, the coil position detection unit 24 is disposed in a state of being directly attached to the subject 200, or is disposed in a room where the endoscope system 1 is installed.

The coil position detection unit 24 detects a magnetic field generated by the position detection coils 23, and transmits a detection signal which corresponds to the detected magnetic field, that is, a position information signal relating to the relative position of the insertion portion 6, inserted into the enteric canal, with respect to the enteric canal, to a shape/position information arithmetic unit 38 of the video processor 3 serving as a control device which will be described later.

In response to the position information signal relating to the insertion portion 6, which is outputted from the coil position detection unit 24, the shape/position information arithmetic unit 38 performs the arithmetic operation of relative position information of the insertion portion 6, in which the position detection coils 23 are arranged, with respect to the subject 200 (enteric canal), and of shape information of the insertion portion 6 in the enteric canal. Note that a configuration may be adopted where a transmission/reception relationship between the position detection coils 23 and the coil position detection unit 24 is reversed. In other words, it may be configured such that a magnetic field generated by the coil position detection unit 24 is received by the position detection coils 23.

The insertion portion position detection unit (magnetic sensor) 25, formed of the position detection coils 23 and the coil position detection unit 24, and the shape/position information arithmetic unit 38 can also detect the direction of the insertion portion 6 in the enteric canal. In other words, by arranging the plurality of position detection coils 23 at the same positions in the longitudinal direction of the insertion portion 6 but in different positions in a circumferential direction, it becomes possible to detect not only the relative position of the insertion portion 6 with respect to the subject 200 but also arrangement and posture information of the insertion portion 6.

The magnetic sensor is adopted as the insertion portion position detection unit 25 in the first embodiment. However, the configuration is not limited to the above. As will be described later in a second embodiment, a shape sensor or an insertion amount sensor may be adopted as the insertion portion position detection unit. Alternatively, the insertion portion position detection unit 25 may adopt an ultrasound method, an optical method, a method which uses an acceleration sensor, or other method. In other words, it is sufficient that the insertion portion position detection unit 25 can detect the position or the relative position of the insertion portion 6 with respect to the subject 200 or with respect to a place, such as a room in which the subject 200 is located.

More specifically, for example, the above-mentioned insertion amount sensor may be a sensor including a rotation amount (torsion amount) sensor when necessary. By detecting the amount of rotation (the amount of torsion) of the insertion portion inserted into the subject (patient), it is possible to more accurately obtain the relative position of the insertion portion with respect to the subject (patient). The insertion amount sensor (including the rotation amount sensor) will be described later in detail as the second embodiment.

<Control Device: Video Processor 3>

The video processor 3 is configured such that a processor, including a CPU, a memory and the like, is caused to execute software read from the memory, thus carrying out the function of respective units in the video processor 3. However, the configuration is not limited to the above. The video processor 3 may be configured of a processor including an electronic circuit that corresponds to the respective units of the video processor 3. Alternatively, the video processor 3 may be configured of a processor including an integrated circuit, such as an FPGA (field programmable gate array), provided with a circuit unit that corresponds to the respective units in the video processor 3.

As shown in FIG. 1, in the first embodiment, the video processor 3 includes an image processing unit 37 that receives an input of an image pickup signal from the image pickup unit 21, and performs a predetermined image processing. The image pickup signal on which the image processing is performed by the image processing unit 37 is outputted to the monitor 5.

In the first embodiment, the video processor 3 acts as the control device by which the present invention is characterized. The control device has a configuration that achieves the function of calculating force information of a pressing force (first force) applied from the insertion portion to the enteric canal, and of obtaining information of a force applied to the subject (the enteric canal) based on the force information and the like and fixed point information, and the function of estimating the effect on the subject (the enteric canal). Hereinafter, the configuration of the video processor 3 as the control device will be described.

In the first embodiment, as shown in FIG. 1, the video processor 3 includes the shape/position information arithmetic unit 38, a first force information calculation unit 30, a second force information determination unit 31, a fixed point setting unit 32, a third force/fourth force information calculation unit 33, a fixed point position information storing unit 34, a subject effect estimation unit 35, and a subject effect recording unit 36. The shape/position information arithmetic unit 38 receives an input of a detection signal (a detection signal relating to the position of the insertion portion 6 or the like) from the insertion portion position detection unit 25, and performs the arithmetic operation of shape information and position information of the insertion portion 6. The first force information calculation unit 30 calculates first force information based on the shape information and the position information from the shape/position information arithmetic unit 38. The second force information determination unit 31 determines the position (second force information) at which the enteric canal receives a reaction force (second force), based on the information from the shape/position information arithmetic unit 38 and the information from the first force information calculation unit 30. The fixed point setting unit 32 sets position information of the fixed points of the enteric canal. The third force/fourth force information calculation unit 33 calculates the magnitudes of a third force and a fourth force related to the second force. The fixed point position information storing unit 34 stores in advance the position information of the fixed points. The subject effect estimation unit 35 estimates the effect on the subject of pressing forces (the second force, the third force, the fourth force) against the enteric canal. The subject effect recording unit 36 records the effect.

In response to the position information signal relating to the insertion portion 6, which is outputted from the coil position detection unit 24 of the insertion portion position detection unit 25, the shape/position information arithmetic unit 38 performs the arithmetic operation of relative position information of the insertion portion 6, in which the position detection coils 23 are arranged, with respect to the subject 200 and of shape information of the insertion portion 6 in the enteric canal. The result of the arithmetic operation is transmitted to the first force information calculation unit 30 disposed downstream of the shape/position information arithmetic unit 38.

Based on the shape information and the position information of the insertion portion 6 in the enteric canal obtained by the shape/position information arithmetic unit 38, the first force information calculation unit 30 calculates the first force information including the position of the point of application of a pressing force (first force) applied from the enteric canal to the insertion portion, the direction of the first force, and the magnitude of the first force. The method for calculating the first force information will be described later in detail.

Based on the position information of the insertion portion 6 in the enteric canal obtained by the shape/position information arithmetic unit 38, and on the position information of the point of application of the first force, applied to the insertion portion 6, which is calculated by the first force information calculation unit 30, the second force information determination unit 31 determines "reaction position: second force information" at which the enteric canal receives the second force, that is, the reaction force of the first force.

The fixed point setting unit 32 sets, as a calculation condition, position information of a first fixed point and a second fixed point being portions of the enteric canal that are partially fixed from outside the enteric canal.

As described above, it is known that the large intestine is an organ which varies in shape, arrangement or the like from person to person and which may particularly change shape due to the lapse of time, the insertion of an instrument or the like. It is also known that the large intestine includes the movable enteric canal and the fixed enteric canal. The sigmoid colon and the transverse colon are classified as the movable enteric canal, which can freely move. The rectum (the upper rectum, the lower rectum), the anal canal, the descending colon, and the ascending colon are classified as the fixed enteric canal.

The applicant of the present invention focuses attention on the presence of the rectum, the anal canal, the descending colon, and the ascending colon each having a part (fixed point) fixed to a predetermined portion inside the body, and provides an endoscope system in which obtaining forces generated at the fixed points of the enteric canal enables estimation of information on the state (the magnitude, the direction) of a pressing force applied from the insertion portion 6 to the movable enteric canal which can freely move, such as the sigmoid colon or the transverse colon, and information on the actually pressed position (reaction position) in the enteric canal, and enables estimation of the effect on the subject at the pressed part (reaction position) based on the information on the state and the information on the actually pressed position.

In the first embodiment, a predetermined portion of a portion of the enteric canal that is partially fixed from outside the enteric canal, for example, of the enteric canal fixed portion where the anal canal (or the upper rectum, the lower rectum) is fixed, is set as a first fixed point. In the same manner, a portion of the enteric canal that is partially fixed from outside the enteric canal, for example, the boundary portion between the sigmoid colon and the descending colon fixed to the fixed portion, is set as a second fixed point. Position information of the two fixed points is set as the calculation condition used in calculating the magnitude of a third force and the magnitude of a fourth force which will be described later.

It is preferable that the fixed point setting unit 32 infer the position of the first fixed point based on the position of the insertion portion 6 detected by the insertion portion position detection unit 25, and set the position of the inferred first fixed point as the calculation condition. The fixed point setting unit 32 may set the position of the second fixed point as the calculation condition based on the detected position of the insertion portion 6, or based on the position of the first fixed point.

Based on the calculation condition set by the fixed point setting unit 32, that is, based on the position information of the first fixed point and the second fixed point, the third force/fourth force information calculation unit 33 (hereinafter, also referred to as "force calculation unit 33") calculates a third force (for example, a force "F1" in FIG. 5) and a fourth force (for example, a force "F2" in FIG. 5) with respect to a second force (for example, a force "F" in FIG. 5), that is, the reaction force of the first force, applied to the enteric canal at the reaction position. The third force is directed toward the first fixed point from the reaction position. The fourth force is directed toward the second fixed point from the reaction position.

Further, the third force/fourth force information calculation unit 33 calculates the magnitude of the third force and the magnitude of the fourth force such that the resultant force of the third force and the fourth force is balanced with the second force. In other words, the third force/fourth force information calculation unit 33 also calculates forces generated at the two fixed points, that is, the forces (for example, forces "F3", "F4" in FIG. 5) generated at the first fixed point and the second fixed point.

The fixed point position information storing unit 34 is formed of a memory unit (memory) that stores in advance the position information of the respective fixed points, such as the above-mentioned first fixed point and second fixed point. When the fixed point setting unit 32 receives the fixed point position information from the fixed point position information storing unit 34, the fixed point setting unit 32 sets the respective fixed points as described above, and sets the position information of the respective fixed points as the calculation condition.

Values estimated based on age, sex, body shape or the like may be used for positions of the fixed points stored in advance. It may be configured such that the positions of corresponding points are measured by sensors at the time of inserting the endoscope to set the measured values as values intrinsic to a subject, and the values are stored in the fixed point position information storing unit 34. An image from the endoscope (an image on which the image processing is performed, when appropriate) may be used for the measurement. For example, a position where the distal end of the endoscope passes through, such as the anus, the bending portion or the like may be used as the fixed point.

Based on the information on "third force" and "fourth force" calculated by the third force/fourth force information calculation unit 33, and on the information on "reaction position" obtained by the second force information determination unit 31, the subject effect estimation unit 35 estimates the effect on the enteric canal (subject) at the enteric canal part pressed by the insertion portion 6 (when the predetermined portion of the enteric canal fixed portion, where the anal canal (or the upper rectum, the lower rectum) is fixed, is set as the first fixed point, and the boundary portion between the sigmoid colon and the fixed portion, where the descending colon is fixed, is set as the second fixed point as described above, the enteric canal part is the sigmoid colon).

The subject effect recording unit 36 records information on the effect on the subject estimated by the subject effect estimation unit 35.

<Summary of Method for Calculating First Force Information>

Next, the summary of the above-mentioned method for calculating first force information by the first force information calculation unit 30 of the first embodiment will be described.

Figure 4:
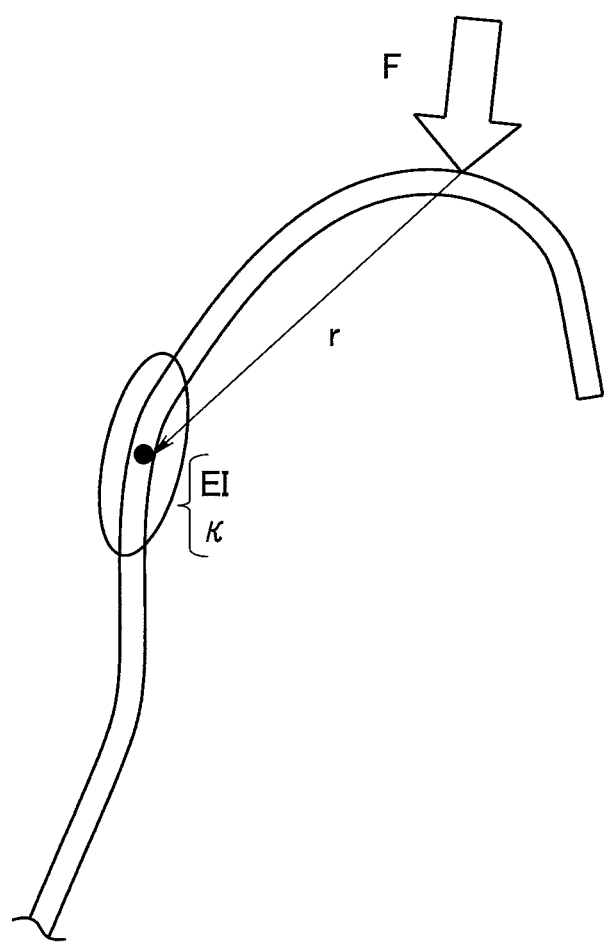
FIG. 4 is an explanatory view showing a concept of calculating a pressing force (first force) applied from the enteric canal to an insertion portion by a first force information calculation unit of the endoscope system of the first embodiment.

FIG. 4 is an explanatory view showing the concept of calculating a pressing force (first force) applied from the enteric canal to the insertion portion by a first force information calculation unit of the endoscope system of the first embodiment.

As described above, in the first embodiment, based on the shape information and the position information of the insertion portion 6 in the enteric canal obtained by the shape/position information arithmetic unit 38, the first force information calculation unit 30 calculates the first force information including the position of the point of application of the pressing force (first force) applied from the enteric canal to the insertion portion, the direction of the first force, and the magnitude of the first force.

The calculation of the first force information is performed based on the dynamic principle, for example. Examples in the calculation of the first force information are as follows. Assume the case where the insertion portion 6 is divided into segments of small unit in the length direction.
(Detection Principle 1)
In the respective segments, "a first internal force Fs estimated from a deformed state of the insertion portion" is substantially equivalent to "a second internal force Ff estimated from a force applied from the outside".
(Detection Principle 2)
In the respective segments, "a first bending moment Mb (bending moment EI·κ (flexural rigidity: EI·curvature κ) in FIG. 4) estimated from the shape information of the insertion portion" is substantially equivalent to "a second bending moment Mf (bending moment r×F ("×" being outer product:) in FIG. 4) estimated from a force applied from the outside".

These principles are based on a static balance, and are based on the assumption that the motion of the insertion portion 6 and the subject 200 is slow. When an insertion device, such as the endoscope 2 of the first embodiment, is inserted, or used in medical diagnosis or medical treatment, the insertion portion 6 and the subject 200 move substantially slowly and hence, it is considered that the insertion portion 6 and the subject 200 satisfy the assumption. Accordingly, result with high accuracy can be supposed.

For the calculation of the first force information, a dynamic principle other than such a static force balance, for example, an equation of dynamic motion may be used, or the combination of the static force balance and another dynamic principle may be used. It may also be possible to use a formula with different physical expressions.

A method for calculating the first force information based on the detection principle 2, which is a specific example of the above-mentioned detection principle 1, will be described later in detail.

Next, the description will be made, with reference to the flowchart shown in FIG. 9 by representing the example shown in FIG. 5, for the calculation of forces by which the enteric canal is pulled by the two fixed portions and forces generated at the enteric canal fixed portions, the forces being generated when the insertion portion 6 of the endoscope system 1 of the first embodiment having the above-mentioned configuration is brought into contact with the respective parts of the enteric canal shown in FIG. 5 to FIG. 8.
<FIG. 5: Case where Distal End Surface of Insertion Portion 6 is Brought into Contact with Portion in the Vicinity of Bent Part of Sigmoid Colon>

Figure 5:
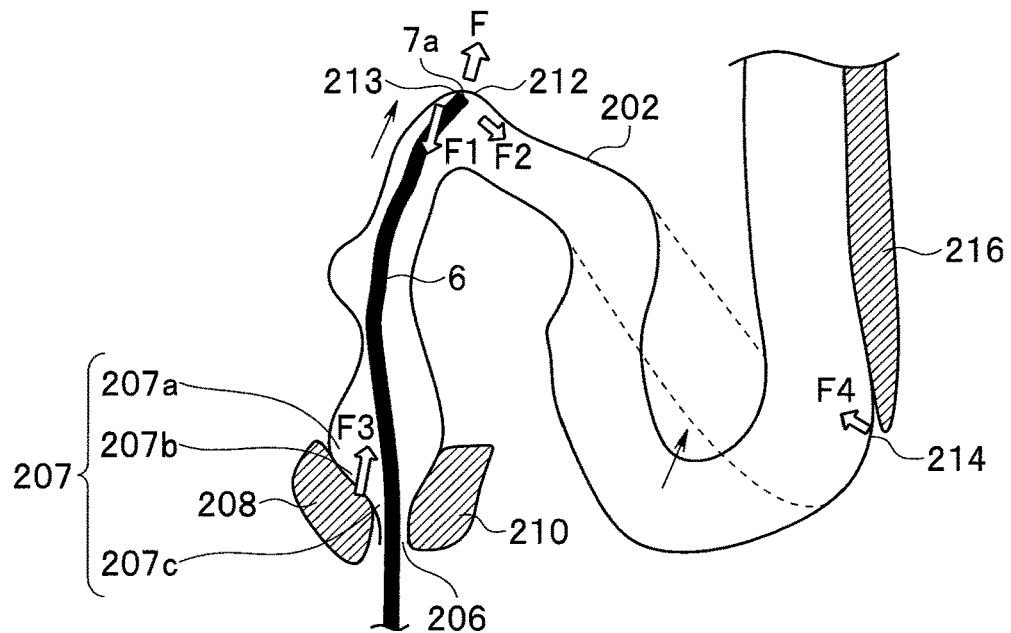
FIG. 5 is an enlarged view of a main part showing the relationship between forces by which the enteric canal is pulled by two fixed portions and forces generated at the enteric canal fixed portions when a distal end portion of the insertion portion presses a sigmoid colon in the endoscope system of the first embodiment.

FIG. 5 is an enlarged view of a main part showing the relationship between forces by which the enteric canal is pulled by the two fixed portions and forces generated at the enteric canal fixed portions when the distal end portion of the insertion portion presses the sigmoid colon in the endoscope system of the first embodiment. FIG. 9 is a flowchart for describing operation of the endoscope system of the first embodiment.

Assume that, as shown in FIG. 5, the insertion portion 6 is now inserted from an anus 206 toward an anal canal 207c, a lower rectum 207b, an upper rectum 207a (hereinafter, the anal canal 207c, the lower rectum 207b, and the upper rectum 207a are also collectively referred to as rectums 207), and a sigmoid colon 202 (it is assumed that the sigmoid colon 202 includes the rectosigmoid. The same applies hereinafter). Thereafter, the insertion portion 6 further moves forward, so the distal end surface 7a of the distal end portion 7 is brought into contact with a portion near the bent part (S-top 212) of the sigmoid colon 202.

At this point of operation, the distal end surface 7a of the insertion portion 6 receives a predetermined pressing force (first force) from a part 213 (near the bent part (S-top 212)) with which the distal end surface 7a is brought into contact. In FIG. 5, enteric canal fixed portions 208, 210 are on both sides of the rectums 207 (the anal canal 207c, the lower rectum 207b, the upper rectum 207a).

The second force "F", which is the reaction force of the first force, is applied to the part 213, and forces (a third force "F1", a fourth force "F2") by which the enteric canal is pulled by the two fixed portions (the enteric canal fixed portion 208 and an SD-J (SD-junction) 214 which will be described later) are generated with respect to the second force.

Assume the state where the distal end surface 7a of the insertion portion 6 is brought into contact with the part 213 near the bent part (S-top 212), thus receiving the predetermined pressing force (first force) from the part 213 as described above. In such a state, the endoscope system 1 of the first embodiment drives the position detection coils 23 (magnetic coils) of the insertion portion position detection unit (magnetic sensor) 25 using the drive unit not shown in the drawing to generate a predetermined magnetic field.

At this point of operation, the coil position detection unit 24 detects the magnetic field generated by the position detection coils 23, and transmits a detection signal which corresponds to the detected magnetic field, that is, a position information signal relating to the position of the insertion portion 6 inserted into the enteric canal, to the shape/position information arithmetic unit 38 of the video processor 3 which will be described later.

Figure 9:
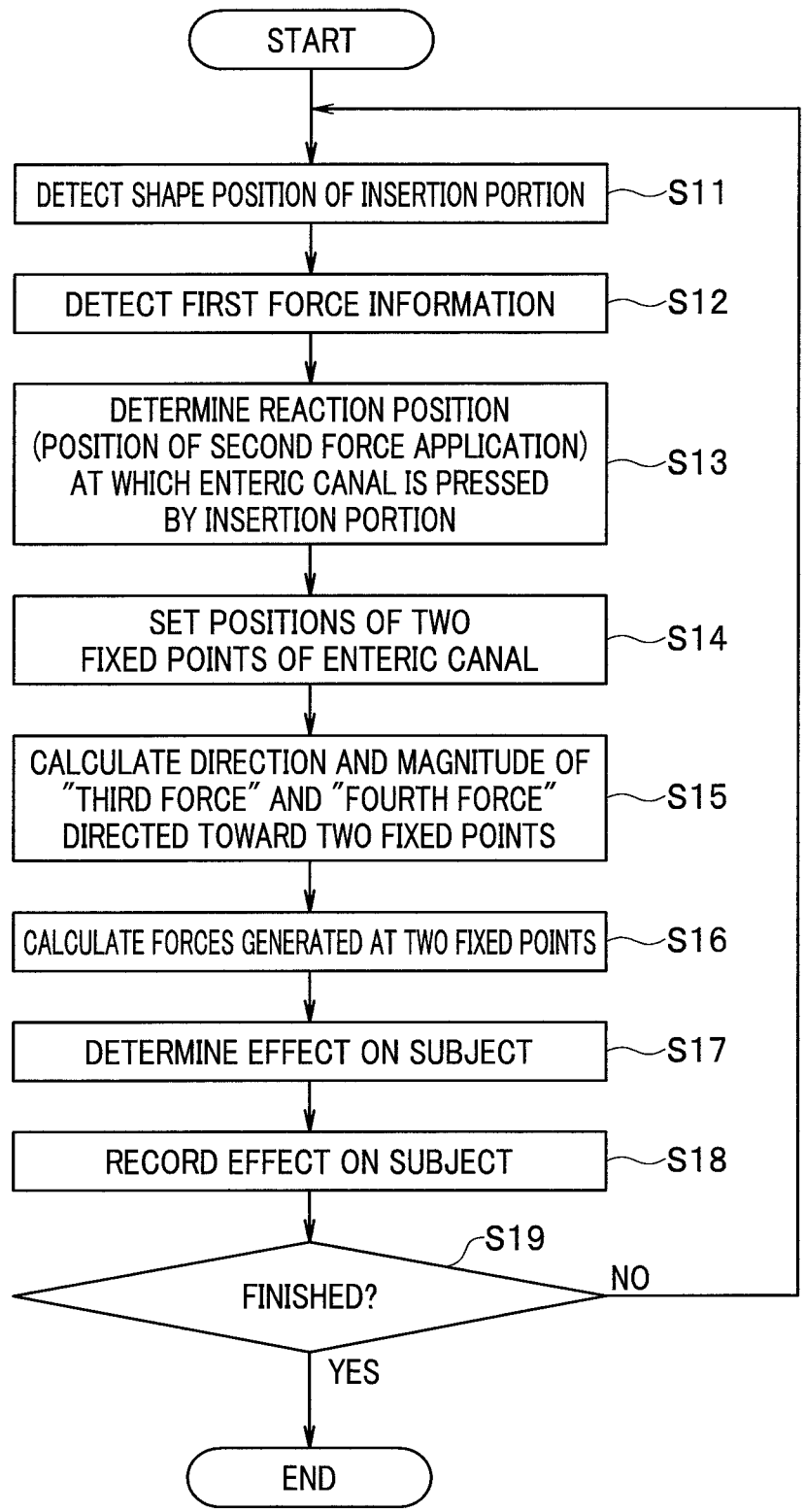
FIG. 9 is a flowchart for describing operation of the endoscope system of the first embodiment.

Further, in response to the position information signal relating to the insertion portion 6, which is outputted from the coil position detection unit 24 of the insertion portion position detection unit 25, the shape/position information arithmetic unit 38 performs the arithmetic operation of relative position information of the insertion portion 6, in which the position detection coils 23 are arranged, with respect to the subject 200 and of shape information of the insertion portion 6 in the enteric canal (step S11 in FIG. 9).

Next, based on the shape information and the position information of the insertion portion 6 in the enteric canal obtained by the shape/position information arithmetic unit 38, the first force information calculation unit 30 calculates the first force information including the position of the point of application of the pressing force (first force) applied from the enteric canal to the insertion portion, the direction of the first force, and the magnitude of the first force (step S12).

Thereafter, based on the position information of the insertion portion 6 in the enteric canal obtained by the shape/position information arithmetic unit 38, and on the position information of the point of application of the first force, applied to the insertion portion 6, which is calculated by the first force information calculation unit 30, the second force information determination unit 31 determines "reaction position" at which the enteric canal receives the second force, that is, the reaction force of the first force (step S13).

In FIG. 5, the position of the point of application of the first force is the distal end surface 7*a*, and "reaction position" of the enteric canal which receives the reaction force of the first force is the part 213.

In the first embodiment, the fixed point setting unit 32 sets, as the calculation condition, the position information of two fixed points, that is the first fixed point and the second fixed point being portions of the enteric canal that are partially fixed from outside the enteric canal (step S14).

In the first embodiment, as shown in FIG. 5, the predetermined portion of the portion of the enteric canal that is partially fixed from outside the enteric canal, for example, of the enteric canal fixed portion 208, where the rectums 207 (the anal canal 207*c*, the lower rectum 207*b*, the upper rectum 207*a*) is fixed, is set as the first fixed point. In the same manner, the portion of the enteric canal that is partially fixed from outside the enteric canal, for example, the SD-J (SD-junction) 214, which is the boundary portion between the sigmoid colon and the descending colon fixed to a fixed portion 216, is set as the second fixed point. The position information of the fixed points is set as the calculation condition used in calculating the magnitude of the third force and the magnitude of the fourth force which will be described later.

The fixed point position information storing unit 34 stores in advance the position information of the respective fixed points, such as the above-mentioned first fixed point and second fixed point. When the fixed point setting unit 32 receives the fixed point position information from the fixed point position information storing unit 34, the fixed point setting unit 32 sets the respective fixed points as described above, and sets the position information of the respective fixed points as the calculation condition.

Next, based on the calculation condition set by the fixed point setting unit 32, that is, based on the position information of the first fixed point and the second fixed point, the third force/fourth force information calculation unit 33 calculates the third force (the force "F1" in FIG. 5) and the fourth force (the force "F2" in FIG. 5) with respect to the second force (the force "F" in FIG. 5), that is, the reaction force of the first force, applied to the enteric canal at the reaction position. The third force is directed toward the first fixed point (the enteric canal fixed portion 208) from the reaction position (the part 213 of the enteric canal in FIG. 5). The fourth force is directed toward the second fixed point (the SD-J (SD-junction) 214) from the reaction position (the part 213) (step S15).

The third force/fourth force information calculation unit 33 calculates the magnitude of the third force and the magnitude of the fourth force such that the resultant force of the third force "F1" and the fourth force "F2" is balanced with the second force "F". In other words, the third force/fourth force information calculation unit 33 calculates forces generated at the two fixed points, that is, a force (a force "F3" in FIG. 5) generated at the first fixed point (for example, the enteric canal fixed portion 208, where the rectums 207 is fixed) and a force (a force "F4" in FIG. 5) generated at the second fixed point (for example, the SD-J (SD-junction) 214 of the descending colon) (step S16).

Thereafter, based on the information on the magnitude, the direction, and the position of the first force calculated by the first force information calculation unit 30, the magnitude and the direction of the second force being the reaction of the first force information, the reaction position of the second force determined by the second force information determination unit 31, and the magnitudes and the directions of the third force and the fourth force calculated by the third force/fourth force information calculation unit 33, the subject effect estimation unit 35 estimates the effect on the enteric canal (subject) at the enteric canal part which is pressed by the insertion portion 6 (when the predetermined portion of the enteric canal fixed portion 208, where the rectums 207 is fixed, is set as the first fixed point, and the SD-J (SD-junction) 214 of the descending colon is set as the second fixed point as described above, the enteric canal part is the sigmoid colon) (step S17).

Further, the subject effect recording unit 36 records information on the effect on the subject estimated by the subject effect estimation unit 35 (step S18), and finishes the processing (step S19).

Figure 6:
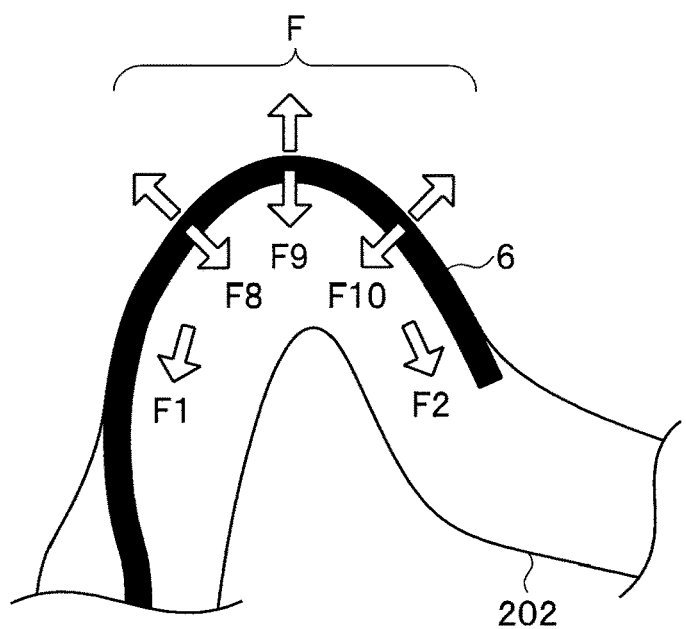
FIG. 6 is an enlarged view of a main part showing a state of forces by which the enteric canal presses the insertion portion when a portion near a bending portion of the insertion portion presses the sigmoid colon in the endoscope system of the first embodiment.

<FIG. 6: Case where Portion Near Bending Portion of the Insertion Portion 6 is Brought into Contact with Portion in the Vicinity of Bent Part of Sigmoid Colon>

FIG. 6 is an enlarged view of a main part showing a state of forces by which the enteric canal presses the insertion portion when a portion near the bending portion of the insertion portion presses the sigmoid colon in the endoscope system of the first embodiment.

As shown in FIG. 6, in the case where the portion near the bending portion 8 of the insertion portion 6 is brought into contact with the enteric canal on the lengthwise side surface of the portion, pressing forces (first forces) are applied from the enteric canal to the insertion portion 6 at a plurality of points or in a distributed manner (see forces "F8", "F9", "F10" in FIG. 6).

Also in the case shown in FIG. 6 where the pressing forces are applied from the enteric canal at the plurality of points or in a distributed manner, second forces (indicated by forces "F" in FIG. 6 for the sake of convenience) being the reaction forces of the first forces (forces "F8", "F9", "F10" in FIG. 6) are respectively applied at the plurality of points.

Further, forces (a third force "F1", a fourth force "F2") by which the enteric canal is pulled by the above-mentioned two fixed portions (the enteric canal fixed portion 208 and the SD-J (SD-junction) 214) are respectively generated with respect to the resultant force of the second forces "F" respectively generated at the plurality of points.

Assume a state where a portion near the bending portion 8 of the insertion portion 6 is brought into contact with the enteric canal on the lengthwise side surface of the portion, thus receiving the pressing forces (first forces) from the enteric canal at the plurality of points or in a distributed manner as described above. Also in such a state, the endoscope system 1 of the first embodiment drives the position detection coils 23 (magnetic coils) of the insertion portion position detection unit (magnetic sensor) 25 using the drive unit not shown in the drawing to generate a predetermined magnetic field.

At this point of operation, in the same manner as the above, the coil position detection unit 24 detects the magnetic field generated by the position detection coils 23, and transmits a detection signal which corresponds to the detected magnetic field, that is, a position information signal relating to the position of the insertion portion 6 inserted into the enteric canal, to the shape/position information arithmetic unit 38 of the video processor 3 which will be described later.

The operation performed thereafter of each of the shape/position information arithmetic unit 38, the first force information calculation unit 30, the second force information determination unit 31, the third force/fourth force information calculation unit 33, the fixed point setting unit 32, the subject effect estimation unit 35, the subject effect recording unit 36 and the like is substantially equivalent to the operation of the corresponding component in the case shown in FIG. 5 where the distal end surface 7*a* of the insertion portion 6 is brought into contact with a portion near the bent part of the sigmoid colon. Therefore, the detailed description will be omitted here.

Figure 7:
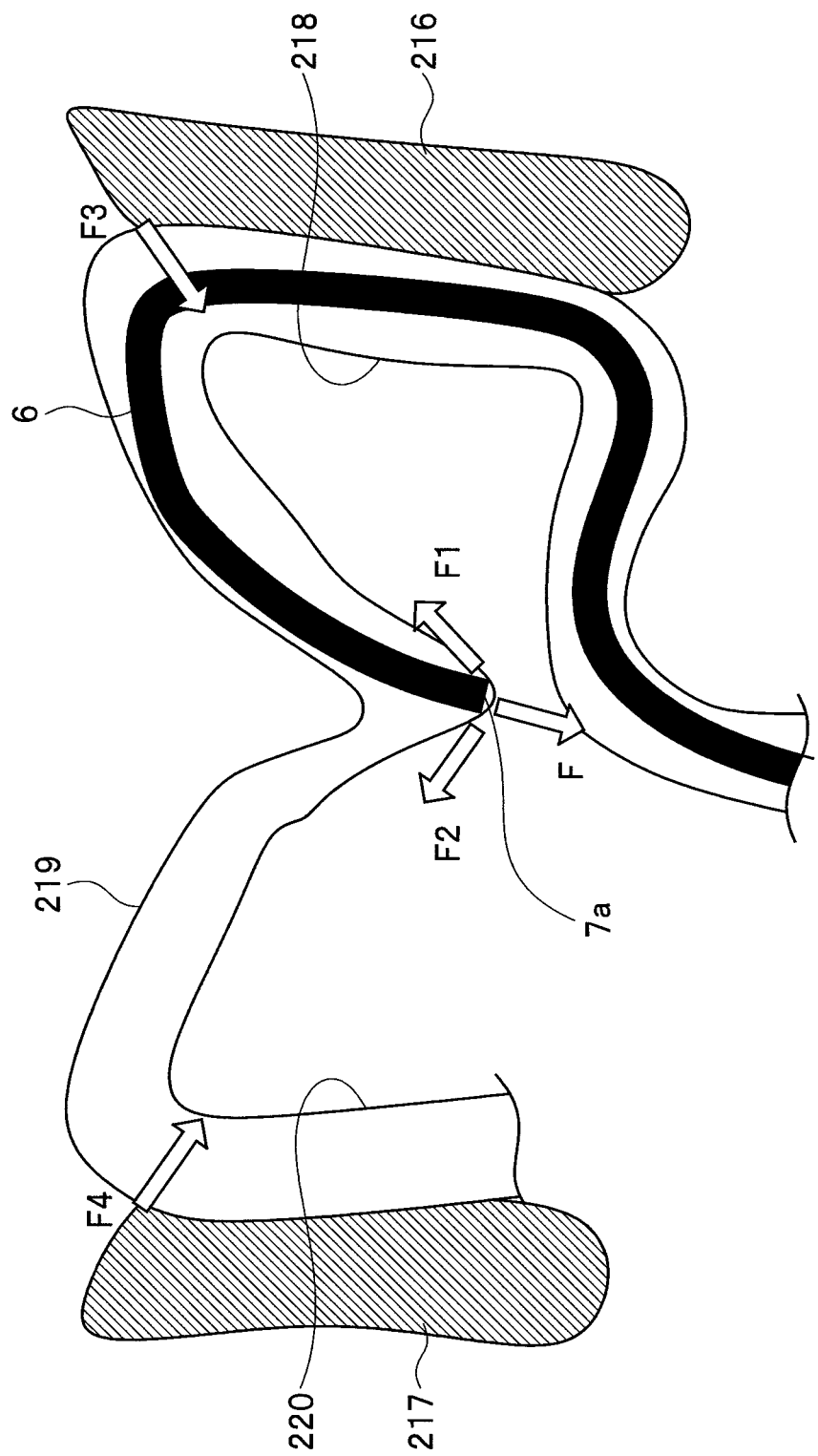
FIG. 7 is an enlarged view of a main part showing the relationship between forces by which the enteric canal is pulled by two fixed portions and forces generated at the enteric canal fixed portions when the distal end portion of the insertion portion presses a transverse colon in the endoscope system of the first embodiment.

<FIG. 7: Case where Distal End of Insertion Portion 6 is Brought into Contact with Portion in the Vicinity of Bent Part of Transverse Colon>

FIG. 7 is an enlarged view of a main part showing the relationship between forces by which the enteric canal is pulled by the two fixed portions and forces generated at the enteric canal fixed portions when the distal end portion of the insertion portion presses the transverse colon in the endoscope system of the first embodiment.

Assume that, as shown in FIG. 7, the distal end portion 7 of the insertion portion 6 now passes through a descending colon 218, and moves beyond the splenic flexure of colon (splenic flexure), so the distal end surface 7*a* of the insertion portion 6 is brought into contact with a portion near the bent part of a transverse colon 219. At this point of operation, the distal end surface 7*a* of the insertion portion 6 receives a predetermined pressing force (first force) from the bent part with which the distal end surface 7*a* is brought into contact.

In FIG. 7, a side surface of the descending colon 218 is fixed by the enteric canal fixed portion 216, and a side surface of an ascending colon 220 is fixed by an enteric canal fixed portion 217.

As shown in FIG. 7, in the same manner as the case where the distal end surface 7*a* of the insertion portion 6 is brought into contact with the bent part of the transverse colon, and the case of the above-mentioned sigmoid colon, a second force "F", which is the reaction force of a first force, is applied to the bent part, and forces (a third force "F1", a fourth force "F2") by which the enteric canal is pulled by two fixed portions (a boundary portion between the transverse colon and the splenic flexure of colon (splenic flexure) of the enteric canal fixed portion 216, where the descending colon 218 is fixed, a boundary portion between the transverse colon and the hepatic flexure of colon (hepatic flexure) of the enteric canal fixed portion 217, where the ascending colon 220 is fixed) are generated with respect to the second force.

Also in the example shown in FIG. 7, the two fixed portions (the boundary portion between the transverse colon and the splenic flexure of colon (splenic flexure) of the enteric canal fixed portion 216, where the descending colon 218 is fixed, the boundary portion between the transverse colon and the hepatic flexure of colon (hepatic flexure) of the enteric canal fixed portion 217, where the ascending colon 220 is fixed) are set as portions of the enteric canal that are partially fixed from outside the enteric canal, and position information of the fixed points is set as the calculation condition used in calculating the magnitude of the third force "F1" and the magnitude of the fourth force "F2".

In the same manner as the above, based on the calculation condition set by the fixed point setting unit 32, that is, based on the position information of the first fixed point and the second fixed point, the third force/fourth force information calculation unit 33 calculates the third force (the force "F1" in FIG. 7) and the fourth force (the force "F2" in FIG. 7) with respect to the second force (the force "F" also in FIG. 7), that is, the reaction force of the first force, applied to the enteric canal at the reaction position. The third force is directed toward the first fixed point (the boundary portion between the transverse colon and the splenic flexure of colon (splenic flexure) of the enteric canal fixed portion 216, where the descending colon 218 is fixed) from the reaction position (the bent part of the transverse colon in FIG. 7). The fourth force is directed toward the second fixed point (the boundary portion between the transverse colon and the hepatic flexure of colon (hepatic flexure) of the enteric canal fixed portion 217, where the ascending colon 220 is fixed) from the reaction position.

In the same manner as the above, the third force/fourth force information calculation unit 33 also calculates forces generated at the two fixed points, that is, a force (a force "F3" in FIG. 7) generated at the first fixed point, and a force (a force "F4" in FIG. 7) generated at the second fixed point.

Thereafter, in the same manner as the above, based on the information on "third force "F1"" and "fourth force "F2"" calculated by the third force/fourth force information calculation unit 33, and on the information on "reaction position" obtained by the second force information determination unit 31, the subject effect estimation unit 35 estimates the effect on the enteric canal (the subject) in the transverse colon against which the insertion portion 6 presses, and the subject effect recording unit 36 records information on the effect on the subject.

Figure 8:
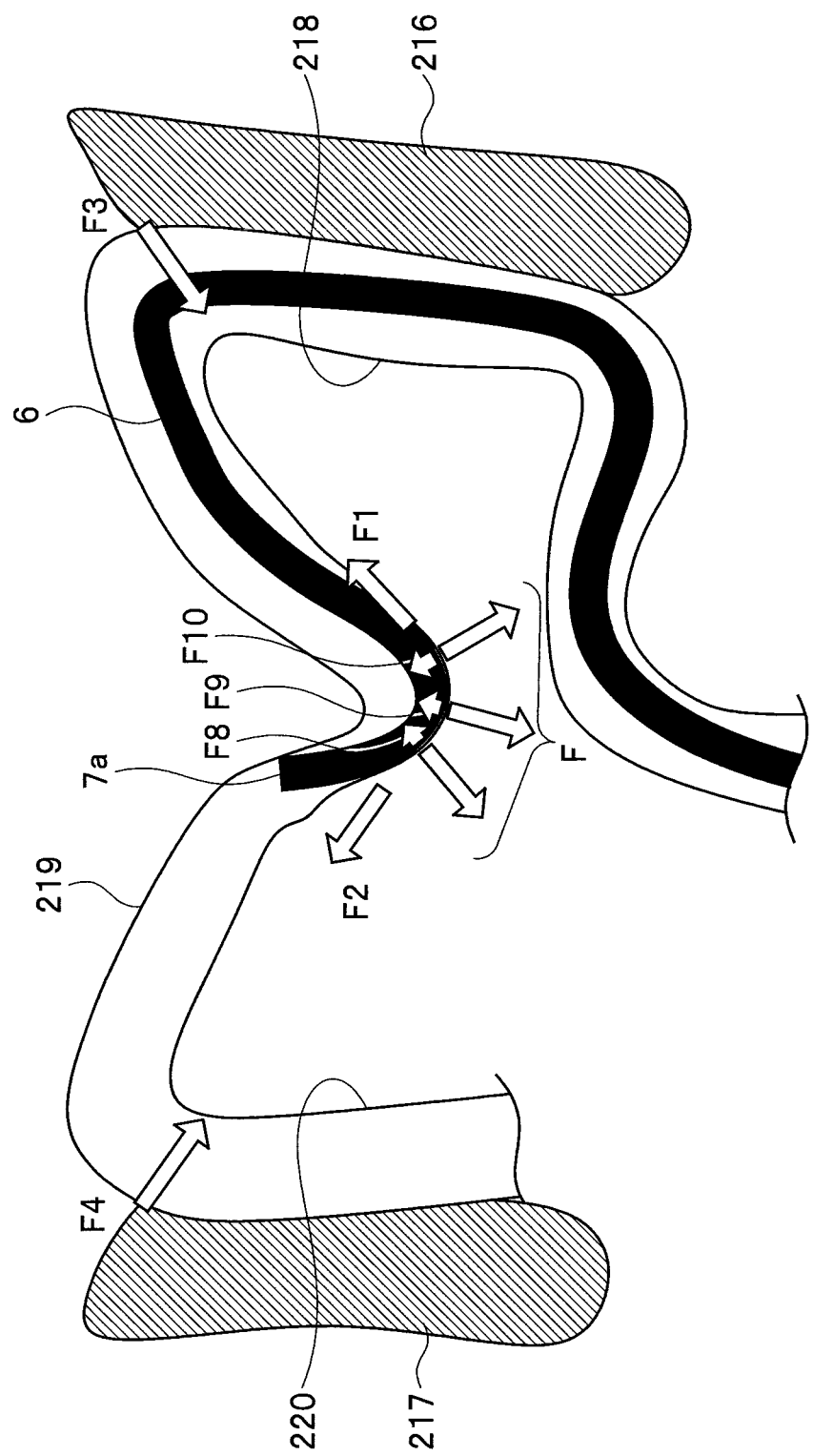
FIG. 8 is an enlarged view of a main part showing the relationship between forces by which the enteric canal is pulled by the two fixed portions and forces generated at the enteric canal fixed portions when the portion near the bending portion of the insertion portion presses the transverse colon in the endoscope system of the first embodiment.

<FIG. 8: Case where Portion Near Bending Portion of Insertion Portion 6 is Brought into Contact with Portion in the Vicinity of Bent Part of Transverse Colon>

FIG. 8 is an enlarged view of a main part showing the relationship between forces by which the enteric canal is pulled by two fixed portions and forces generated at the enteric canal fixed portions when a portion near the bending portion of the insertion portion presses the transverse colon in the endoscope system of the first embodiment.

Also in the example shown in FIG. 8, in the same manner as the example shown in FIG. 6, in the case where the portion near the bending portion 8 of the insertion portion 6 is brought into contact with the enteric canal on the lengthwise side surface of the portion, pressing forces (first forces) are applied from the enteric canal to the insertion portion 6 at a plurality of points or in a distributed manner (see forces "F8", "F9", "F10" in FIG. 8).

Also in the case shown in FIG. 8 where the pressing forces are applied from the enteric canal at the plurality of points or in a distributed manner, second forces (indicated by forces "F" in FIG. 8 for the sake of convenience) being reaction forces of the first forces (the forces "F8", "F9", "F10" in FIG. 8) are respectively applied at the plurality of points.

Further, forces (a third force "F1", a fourth force "F2") by which the enteric canal is pulled by the above-mentioned two fixed portions (the boundary portion between the transverse colon and the splenic flexure of colon (splenic flexure) of the enteric canal fixed portion 216, where the descending colon 218 is fixed, the boundary portion between the transverse colon and the hepatic flexure of colon (hepatic flexure) of the enteric canal fixed portion 217, where the ascending colon 220 is fixed) are generated with respect to the resultant force of the second forces "F" respectively generated at the plurality of points.

Assume a state where a portion near the bending portion 8 of the insertion portion 6 is brought into contact with the enteric canal on the lengthwise side surface of the portion, thus receiving the pressing forces (first forces) from the enteric canal at the plurality of points or in a distributed manner as described above. Also in such a state, the endoscope system 1 of the first embodiment drives the position detection coils 23 (magnetic coils) of the insertion portion position detection unit (magnetic sensor) 25 using the drive unit not shown in the drawing to generate a predetermined magnetic field.

At this point of operation, in the same manner as the above, the coil position detection unit 24 detects the magnetic field generated by the position detection coils 23, and transmits a detection signal which corresponds to the detected magnetic field, that is, a position information signal relating to the position of the insertion portion 6 inserted into the enteric canal, to the shape/position information arithmetic unit 38 of the video processor 3 which will be described later.

The operation performed thereafter of each of the shape/position information arithmetic unit 38, the first force information calculation unit 30, the second force information determination unit 31, the third force/fourth force information calculation unit 33, the fixed point setting unit 32, the subject effect estimation unit 35, the subject effect recording unit 36 and the like is substantially equivalent to the operation of the corresponding component in the case shown in FIG. 7 where the distal end surface 7a of the insertion portion 6 is brought into contact with a portion near the bent part of the transverse colon. Therefore, the detailed description will be omitted here.

As has been described heretofore, the endoscope system 1 of the first embodiment focuses attention on the presence of the rectum (the upper rectum, the lower rectum), the anal canal, the descending colon, and the ascending colon each having a part (fixed point) fixed to a predetermined portion inside the body. Therefore, it is possible to provide an endoscope system in which obtaining forces generated at the fixed points of the enteric canal enables estimation of information on the state (the magnitude, the direction) of a pressing force applied from the insertion portion 6 to the movable enteric canal which can freely move, such as the sigmoid colon or the transverse colon, and information on the actually pressed position (reaction position) in the enteric canal, and enables estimation of the effect on the subject at the pressed part (reaction position) based on the information on the state and the information on the actually pressed position.

Next, a method for calculating the first force information based on the detection principle 2, which is a specific example of the above-mentioned detection principle 1, will be described in detail.

Figure 10:
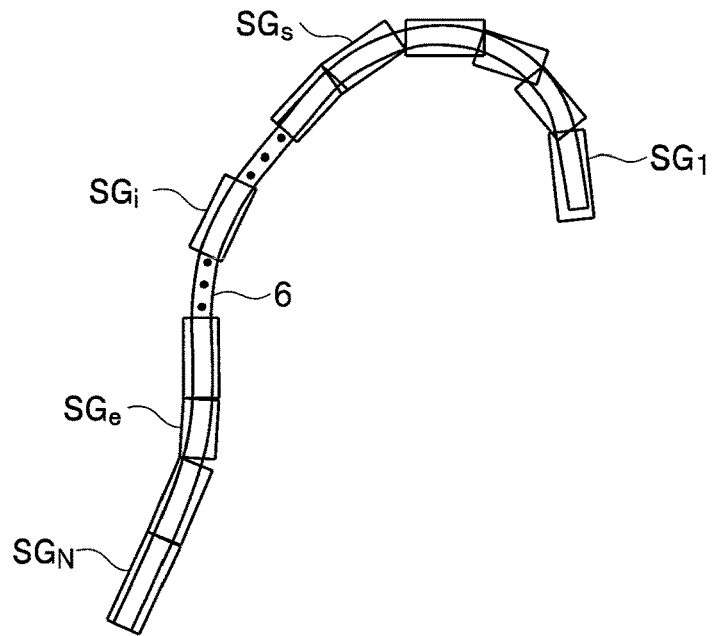
FIG. 10 is a view for describing a concept of segments of the insertion portion of the endoscope system of the first embodiment.

FIG. 10 shows the insertion portion 6 of the endoscope 2 in a state of being divided into segments. Assume that, in FIG. 10, there are N number of segments ranging from a segment 1 on the distal end side of the insertion portion 6 to a segment N on the hand side. Of these segments, Ns number of segments ranging from a segment SGs to a segment SGe are targets of calculation.

In the calculation of the first force information based on a static balance, the first force information calculation unit 30 calculates, for each segment, the first bending moment Mb (bending moment EI·κ (flexural rigidity: EI·curvature κ) in FIG. 4) estimated from the shape-information from the shape/position information arithmetic unit 38, and the second bending moment Mf (bending moment r×F ("×" being outer product:) in FIG. 4) estimated from a force applied from the outside. Such calculations give conditional expressions, where the first bending moment Mb is substantially equivalent to the second bending moment Mf, the number of conditional expressions being equivalent to the number of segments Ns of the insertion portion 6 on which the calculation is performed.

In the first force information to be calculated, there are variables, the number of which is equal to the product of the number of forces Nf and the number of obtaining information contents Nc, that is, Nf×Nc.

When the following equation is established, the value of the variable can be obtained uniquely.

the number of conditional expressions($Ns$)=the number of variables($Nf \times Nc$)

When the following expression is established, the value of the variable cannot be obtained uniquely, so the combination of solutions of variables considered applicable is obtained. Usually, the combination of solutions is obtained by an optimization technique, in which specific evaluation expressions take minimum values or maximum values.

the number of conditional expressions($Ns$)>the number of variables($Nf \times Nc$)

The first force information calculation unit 30 obtains, in other words estimates, the first bending moment Mb from the value of flexural rigidity and shape information, for example, for each segment of the insertion portion 6. The shape information is acquired from the shape/position information arithmetic unit 38.

For the sake of simplification, a calculation method in the case of two dimensions will be described.

Assume that the respective segments have a rectilinear shape when a bending moment is not applied to the segments. However, a portion of the bending portion 8 is bendable in response to a bending operation, so there may be a case where the portion of the bending portion 8 is not in a rectilinear shape when no bending moment is applied by an external force. Therefore, with respect to such a portion, a state where an external force is not applied is used as the reference, and the first bending moment Mb is obtained based on the change from such a state. Note that the bending portion 8 may be excluded from segments on which the arithmetic operation is performed, for the sake of simplification.

Figure 11:
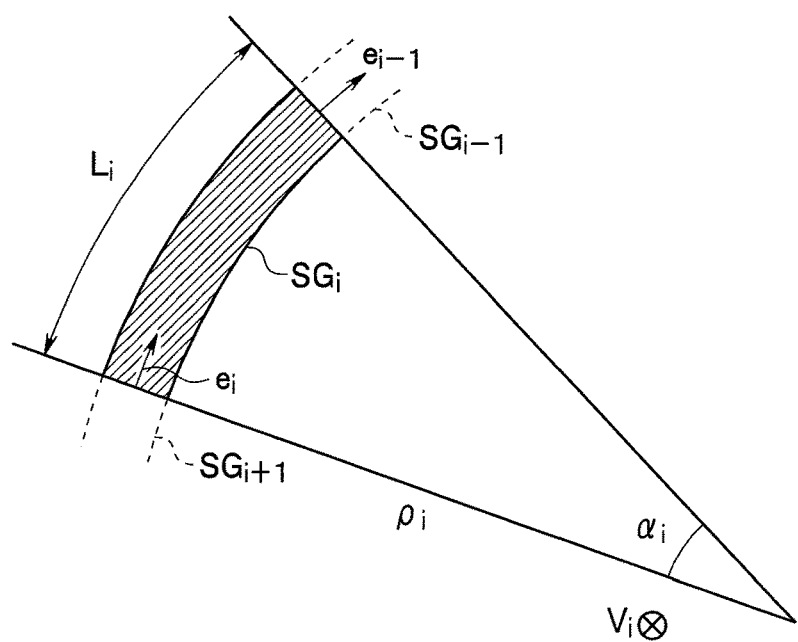
FIG. 11 is a view showing one example of one segment of the insertion portion of the endoscope system of the first embodiment.

The curved shape of a segment $SG_i$, which is the i-th segment, is shown in FIG. 11.

The shape of the segment $SG_i$ approximates an arc.

Definitions are given as follows. The suffix "i" corresponds to the segment $SG_i$.

bending moment estimated from shape: $Mb_i$
Young's modulus: $E_i$
second moment of area: $I_i$
direction vector of segment $SG_i$: $e_i$
where the direction vector $e_i$ is a direction vector at a connecting portion between a segment $SG_{i+1}$ and the segment $SG_i$, the direction vector $e_i$ being directed toward a segment $SG_{i-1}$
direction vector perpendicular to paper surface: $V_i$
curvature: $\chi_i$ ($=1/\rho_i$)
where $\rho_i$ denotes radius of curvature
flexural rigidity: $G_i$ ($=E_i \cdot I_i$)

In such a state, the following relationship can be established for a segment $SG_i$ based on mechanics of materials.

$$Mb_i = E_i / \rho_i \cdot I_i \qquad \text{equation 1}$$

$$\alpha_1 = L_i / \rho_i \qquad \text{equation 2}$$

where $\alpha_i$ denotes an angle [rad], and $L_i$ denotes the length of the segment $SG_i$ The following relationship can be derived from the equation 1 and the equation 2.

$$Mb_i = (\alpha_i / L_i) \cdot (E_i \cdot I_i) = \chi_i \cdot G_i \qquad \text{equation 3}$$

where "$E_i \cdot I_i = G_i$" is referred to as flexural rigidity

The equation 3 can obtain the first bending moment Mb at the segment $SG_i$ estimated from a curved shape or shape information.

$G_i$ may slightly vary according to the magnitude of curvature $\chi_i$. Therefore, $G_i$ may be assumed and used as a constant. Alternatively, $G_i$ may be assumed and used as the variable of curvature $\chi_i$ if an exact value is required.

In the two dimensions, assume that bending moment $Mb_i > 0$ and angle $\alpha_i > 0$ are established when the segment $SG_{i-1}$ side close to the distal end of the insertion portion 6 is bent in a counterclockwise direction.

The first force information calculation unit 30 obtains or estimates the second bending moment Mf generated at each segment of the insertion portion 6, and caused by a force applied from the outside.

For the sake of simplification, a specific calculation will be described from a case where one force acts on the insertion portion 6.

Figure 12:
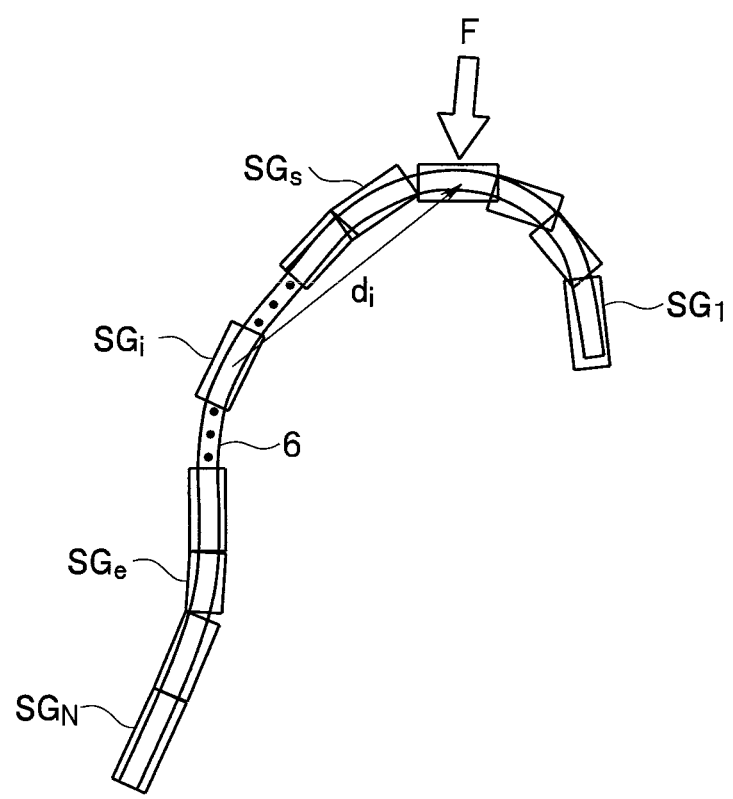
FIG. 12 is a view showing a pressing force F applied to the insertion portion from the subject and a vector $d_i$ from the center of a segment $SG_i$ to a position at which the pressing force F is applied in the endoscope system of the first embodiment.

In FIG. 12, a second bending moment $Mf_i$ applied to the segment $SG_i$ by an external force becomes as follows in terms of dynamics.

<<In the Case of Two Dimensions (XY Coordinate)>>

In this case, when the position at which a pressing force F, which is a vector, is applied is on the distal end side of the position of the segment $SG_i$, the second bending moment $Mf_i$ is as follows. Note that the second bending moment $Mf_i$ is a scalar, and takes a positive value when the second bending moment $Mf_i$ is a bending moment in the counterclockwise direction.

$$Mf_i = z \text{ component of}(d_i \times F) \quad \text{equation 4a}$$

where

"×": outer product $d_i$: vector from center of segment SG; to position at which pressing force F is applied $Mf_i = |d_i \times F|$ (absolute value) may also be adopted instead.

When the position at which the pressing force F is applied is on the hand side of the position of the segment $SG_i$, the second bending moment $Mf_i$ is as follows.

$$Mf_i = 0 \quad \text{equation 4b}$$

The equation 4b is a scalar.

<<In the Case of Three Dimensions>>

In this case, when the position at which a pressing force F, which is a vector, is applied is on the distal end side of the position of the segment $SG_i$, the second bending moment $Mf_i$ is as follows. Note that the second bending moment $Mf_i$ is a vector.

$$Mf_i = d_i \times F \quad \text{equation 4c}$$

When the position at which the pressing force F is applied is on the hand side of the position of the segment $SG_i$, the second bending moment $Mf_i$ is as follows.

$$Mf_i = 0 \quad \text{equation 4d}$$

The equation 4d is a 0 vector, which means a vector of magnitude 0.

In the case where a plurality of forces act, it is sufficient to calculate the resultant force of the plurality of forces for a pressing force $F_j$ applied at the position on the distal end side of the position of the segment $SG_i$. In the case where a force is a distributed load, as will be described later, it is sufficient to consider that forces are concentrated on a plurality of specific points.

<<In the Case of Two Dimensions (XY Coordinate)>>

In this case, the second bending moment $Mf_i$ is as follows.

$$Mf_i = z \text{ component of } [\Sigma(d_{ij} \times F_j)] \quad \text{equation 5a}$$

However, only forces on the distal end side of the position of the segment $SG_i$ are calculated where $F_j$: external force (vector)

"×": outer product $Mf_i = |\Sigma(d_{ij} \times F_j)|$ (absolute value) may be adopted instead.

<<In the Case of Three Dimensions>>

In this case, the second bending moment $Mf_i$ is as follows.

$$Mf_i = \Sigma(d_{ij} \times F_j) \quad \text{equation 5b}$$

However, only forces on the distal end side of the position of the segment $SG_i$ are calculated.

The first force information calculation unit 30 calculates, as first force information, at least required information of the position, the direction, and the magnitude of a force based on the relationship $Mf_i \cong Mb_i$ between a first bending moment $Mb_i$ and the second bending moment $Mf_i$. For example, at least one of the position at which a pressing force F or $F_j$ is applied, the direction of the pressing force F or $F_j$, and the magnitude of the pressing force F or $F_j$ is calculated.

With the use of the technique described above, the first force information calculation unit 30 calculates the first force information relating to the force applied to the insertion portion 6. Further, in the first embodiment, the first force information is outputted to the second force information determination unit 31.

As has been described heretofore, the endoscope system 1 of the first embodiment focuses attention on the presence of the rectum (the upper rectum, the lower rectum), the anal canal, the descending colon, and the ascending colon each having a part (fixed point) fixed to a predetermined portion inside the body. Therefore, it is possible to provide an endoscope system in which obtaining forces generated at the fixed points of the enteric canal enables estimation of information on the state (the magnitude, the direction) of a pressing force applied from the insertion portion 6 to the sigmoid colon or the transverse colon, which is the movable enteric canal which can freely move, and information on the actually pressed position (reaction position) in the enteric canal, and enables estimation of the effect on the subject at the pressed part (reaction position) based on the information on the state and the information on the actually pressed position.

Second Embodiment

Next, a second embodiment of the present invention will be described.

Figure 13:
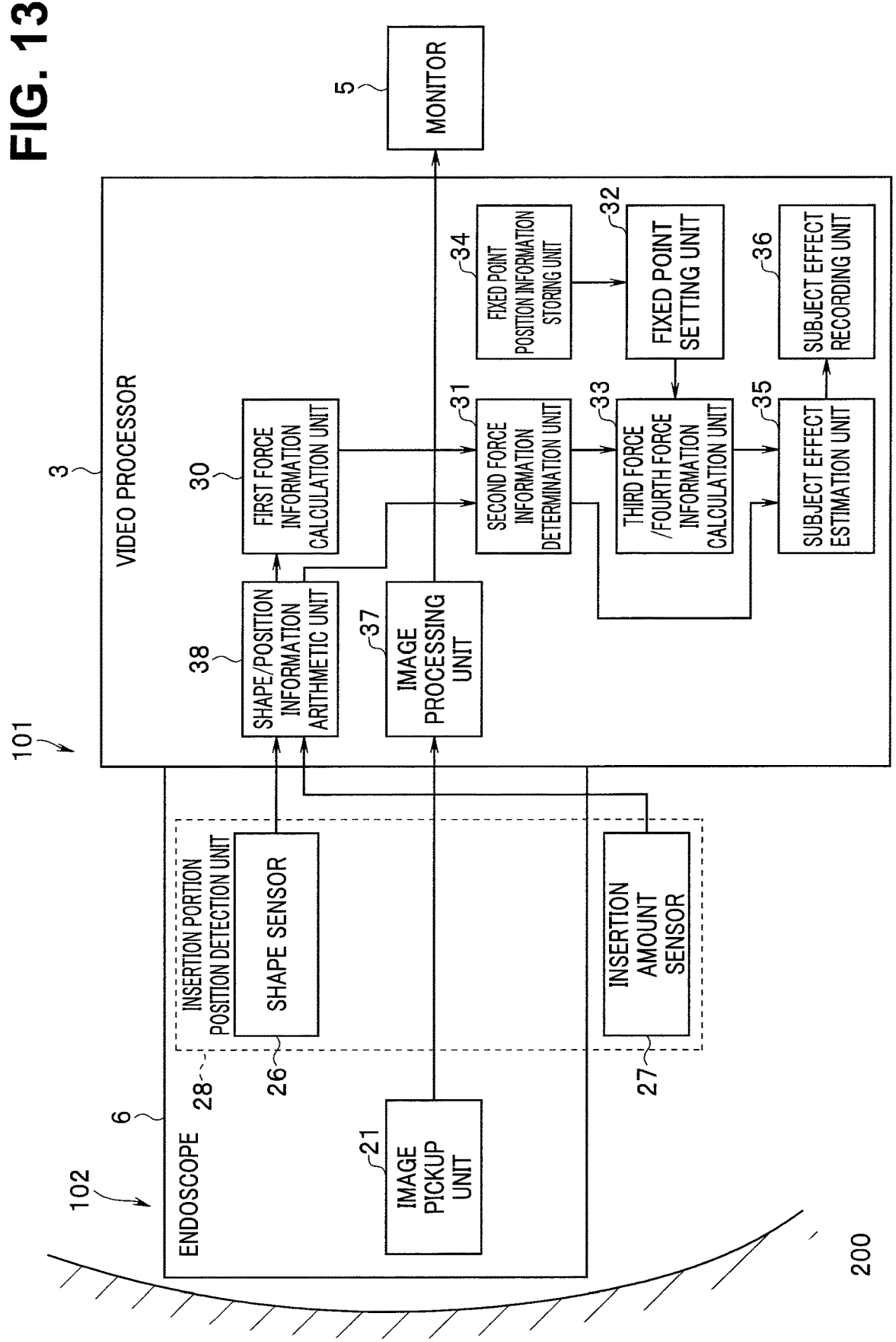
FIG. 13 is a block diagram showing a configuration of an endoscope system of a second embodiment of the present invention.
Figure 14:
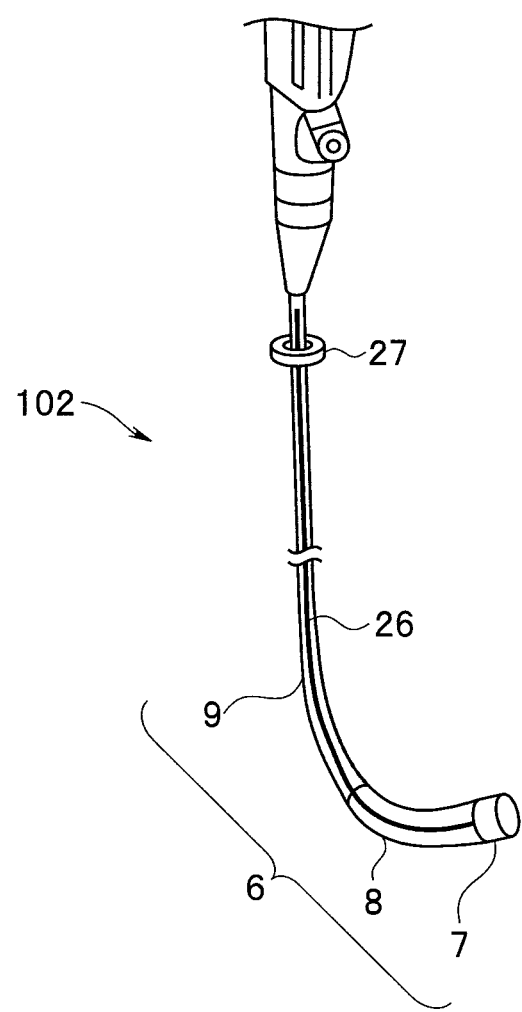
FIG. 14 is an external appearance view of a main part showing a configuration of an insertion portion position detection unit (a shape sensor and an insertion amount sensor) of the endoscope system of the second embodiment.
Figure 15:
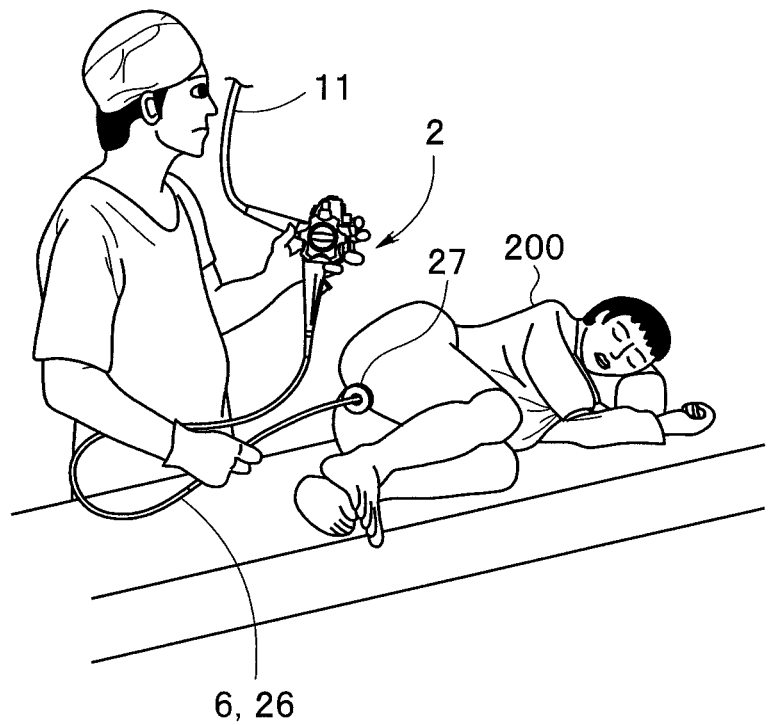
FIG. 15 is an explanatory view showing a state of inserting the endoscope into the subject in the endoscope system of the second embodiment.

FIG. 13 is a block diagram showing a configuration of an endoscope system of the second embodiment of the present invention. FIG. 14 is an external appearance view of a main part showing a configuration of an insertion portion position detection unit (a shape sensor and an insertion amount sensor) of the endoscope system of the second embodiment. Further, FIG. 15 is an explanatory view showing a state of inserting an endoscope into the subject in the endoscope system of the second embodiment.

In the above-mentioned endoscope system 1 of the first embodiment, the insertion portion position detection unit 25, which detects the position of the insertion portion 6 inserted into the enteric canal and which outputs a detection signal, is configured of the magnetic sensor including the position detection coils 23 and the coil position detection unit 24. However, in an endoscope system 101 of the second embodiment, the insertion portion position detection unit is configured of a shape sensor 26, which is provided in the insertion portion 6 of an endoscope 102 and which detects the shape of the insertion portion, and an insertion amount sensor 27, which is provided outside the insertion portion 6 of the endoscope 102 and which detects the insertion length of the insertion portion 6 inserted into the subject 200 during an operation, an inspection or the like.

Other components are substantially equivalent to the corresponding components in the first embodiment and hence, only points which make the second embodiment different from the first embodiment will be described, and the description of the same components will be omitted.

As shown in FIG. 13, the endoscope system 101 of the second embodiment includes an insertion portion position detection unit 28 formed of the shape sensor 26 and the insertion amount sensor 27, the shape sensor 26 being provided in the insertion portion 6 of the endoscope 102, the insertion amount sensor 27 being provided outside the insertion portion 6.

The shape sensor 26 is a sensor that detects the shape of the insertion portion 6 and, as shown in FIG. 14, is provided inside the whole length of the insertion portion 6. Further, a detection signal relating to the shape of the insertion portion detected by the shape sensor 26 is outputted to the shape/position information arithmetic unit 38 of the video processor 3.

The insertion amount sensor 27 is a sensor for acquiring an insertion amount, which is the amount by which the insertion portion 6 is inserted into the enteric canal of the subject 200, and the amount of rotation (the amount of torsion) of the insertion portion 6. In the second embodiment, the insertion amount sensor 27 carries out the function of detecting the relative position of the insertion portion 6 with respect to the subject (patient) 200.

As shown in FIG. 14 and FIG. 15, the insertion amount sensor 27 has a substantially ring shape having a hollow portion that allows the insertion of the insertion portion 6. The shape of the insertion amount sensor 27 is not limited to a simple ring shape. A specific configuration adopted in the second embodiment will be described later in detail.

FIG. 14 schematically shows only a state where the insertion portion 6 is inserted into the hollow portion of the insertion amount sensor 27. After the insertion amount sensor 27 is mounted on the subject 200 as shown in FIG. 15, the insertion amount sensor 27 allows the insertion of the insertion portion 6 to detect the relative position of the insertion portion 6 with respect to the subject (patient) 200.

Figure 16:
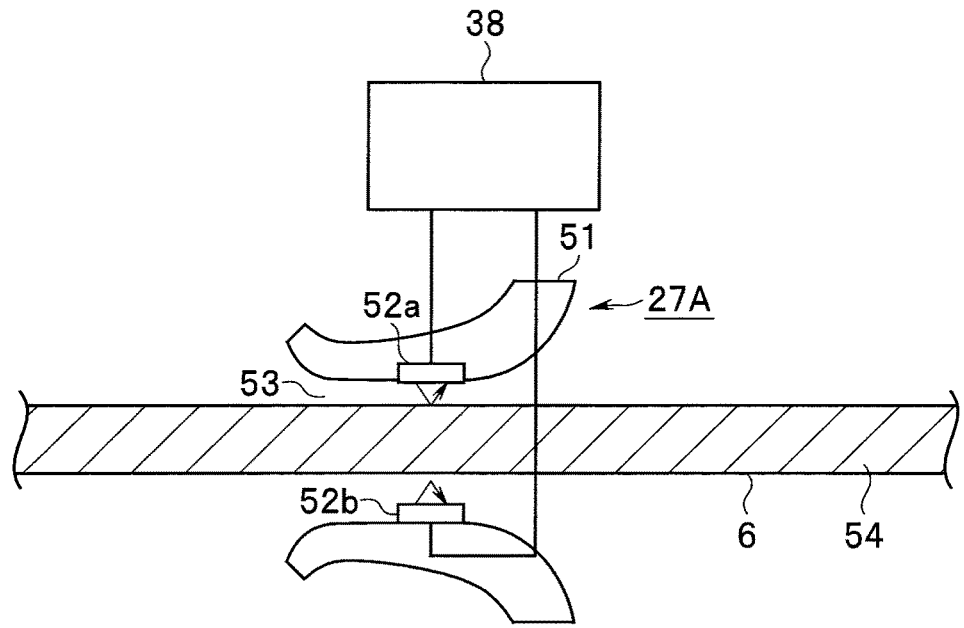
FIG. 16 is an external appearance side view of a main part showing one constitutional example of an insertion amount sensor of the endoscope system of the second embodiment.

FIG. 16 is an external appearance side view of a main part showing an insertion amount sensor 27A, which is one constitutional example of the insertion amount sensor of the endoscope system of the second embodiment.

As shown in FIG. 16, the insertion amount sensor 27A includes a mouthpiece 51 having a hollow opening portion 53 that allows the insertion of the insertion portion 6. In this example, the insertion portion 6 is configured in the form of a scope tube where a 2D encoder pattern 54 is formed on the outer periphery of the insertion portion 6.

The mouthpiece 51 includes an insertion amount detection encoder head 52a and a rotation amount (torsion amount) detection encoder head 52b at positions that face the outer peripheral surface of the insertion portion 6 inserted into the hollow opening portion 53.

When the insertion portion 6 is inserted into the hollow opening portion 53 of the mouthpiece 51, the insertion amount detection encoder head 52a detects the amount of movement in the insertion direction of the 2D encoder pattern 54 formed on the outer peripheral surface of the insertion portion 6, thus detecting the amount of insertion of the insertion portion 6 in the insertion direction.

Further, a signal relating to the amount of insertion of the insertion portion 6 detected by the insertion amount detection encoder head 52a is outputted to the shape/position information arithmetic unit 38 of the video processor 3.

Whereas when the insertion portion 6 is inserted into the hollow opening portion 53 of the mouthpiece 51, the rotation amount detection encoder head 52b detects the amount of torsion in the rotational direction of the 2D encoder pattern 54 formed on the outer peripheral surface of the insertion portion 6, thus detecting the amount of rotation (the amount of torsion) of the insertion portion 6.

A signal relating to the amount of rotation (the amount of torsion) of the insertion portion 6 detected by the rotation amount detection encoder head 52b is also outputted to the shape/position information arithmetic unit 38 of the video processor 3.

Figure 17:
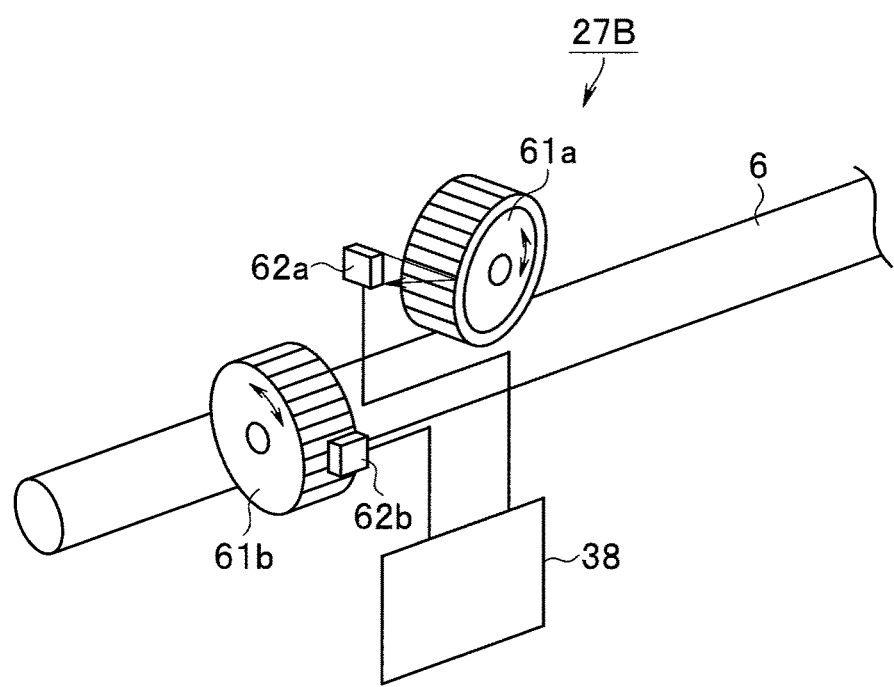
FIG. 17 is an external appearance perspective view of a main part showing another constitutional example of the insertion amount sensor of the endoscope system of the second embodiment.

FIG. 17 is an external appearance perspective view of a main part showing an insertion amount sensor 27B which is another constitutional example of the insertion amount sensor of the endoscope system of the second embodiment.

The insertion amount sensor 27B includes a mouthpiece (the illustration of the mouthpiece is omitted in FIG. 17) having a hollow opening portion, which is similar to the hollow opening portion shown in FIG. 16 described above and which allows the insertion of the insertion portion 6.

The mouthpiece of the insertion amount sensor 27B is provided with an insertion amount detection roller 61a and a rotation amount detection roller 61b. The insertion amount detection roller 61a is brought into contact with the outer peripheral surface of the insertion portion 6 inserted into the hollow opening portion, and rotates with the movement of the insertion portion 6 in the insertion direction. The rotation amount detection roller 61b is brought into contact with the outer peripheral surface of the insertion portion 6 in the same manner, and rotates with the rotation of the insertion portion 6 in the twist direction.

The outer peripheral surface of the insertion amount detection roller 61a has grooves having a linear knurled shape for detecting the amount of rotation of the roller, and an insertion amount detection encoder head 62a is provided at a position that faces the knurled groove.

The outer peripheral surface of the rotation amount detection roller 61b also has grooves having a linear knurled shape for detecting the amount of rotation of the roller, and a rotation amount (torsion amount) detection encoder head 62b is provided at a position that faces the knurled groove.

When the insertion portion 6 is inserted into the hollow opening portion of the mouthpiece, the insertion amount detection encoder head 62a detects the amount of rotation of the insertion amount detection roller 61a, thus detecting the amount of insertion of the insertion portion 6 in the insertion direction.

A signal relating to the amount of insertion of the insertion portion 6 detected by the insertion amount detection encoder head 62a is outputted to the shape/position information arithmetic unit 38 of the video processor 3 in the same manner as the above.

When the insertion portion 6 is inserted into the hollow opening portion of the mouthpiece, the rotation amount detection encoder head 62b also detects the amount of rotation of the rotation amount detection roller 61b, thus detecting the amount of rotation (the amount of torsion) of the insertion portion 6.

A signal relating to the amount of rotation (the amount of torsion) of the insertion portion 6 detected by the rotation amount detection encoder head 62*b* is also outputted to the shape/position information arithmetic unit 38 of the video processor 3.

In the second embodiment, the detection of an amount of insertion or an amount of rotation by the encoder is given as an example. However, the detection is not limited to the above. For example, it may be possible to adopt an input optical mouse for a personal computer or the like, or means/method that detects the motion of image, such as a so-called optical flow.

Returning to FIG. 15, in the endoscope system including a large intestine endoscope as in the case of the second embodiment, during an operation or an inspection, the insertion amount sensor 27A or the insertion amount sensor 27B having the above-mentioned configuration is set on the anus of the subject (patient) 200, and the insertion portion 6 is inserted into the hollow opening portion. Thereafter, the amount of insertion and/or the amount of rotation of the insertion portion 6 are measured, and signals relating to the amount of insertion and/or the amount of rotation are outputted to the shape/position information arithmetic unit 38.

In the second embodiment, the shape/position information arithmetic unit 38 can calculate the position of the insertion portion 6 in the enteric canal based on the information on the amount of insertion and/or the amount of rotation of the insertion portion 6 measured by the above-mentioned insertion amount sensor 27A (see FIG. 16) or insertion amount sensor 27B (see FIG. 17), and on the information on the shape of the insertion portion 6 obtained by the shape sensor 26.

Other components, the operation, and advantageous effects are substantially equivalent to those in the above-mentioned first embodiment and hence, the repeated description will be omitted here.

As has been described heretofore, in the same manner as the first embodiment, the endoscope system 101 according to the second embodiment can also provide an endoscope system that estimates information on the state (the magnitude, the direction) of a pressing force applied from the insertion portion 6 to the sigmoid colon or the transverse colon, which is the movable enteric canal which can freely move, and information on the actually pressed position (reaction position) in the enteric canal, and that enables estimation of the effect on the subject at the pressed part (reaction position) based on the information on the state and the information on the actually pressed position.

Third Embodiment

Next, a third embodiment of the present invention will be described.

Figure 18:
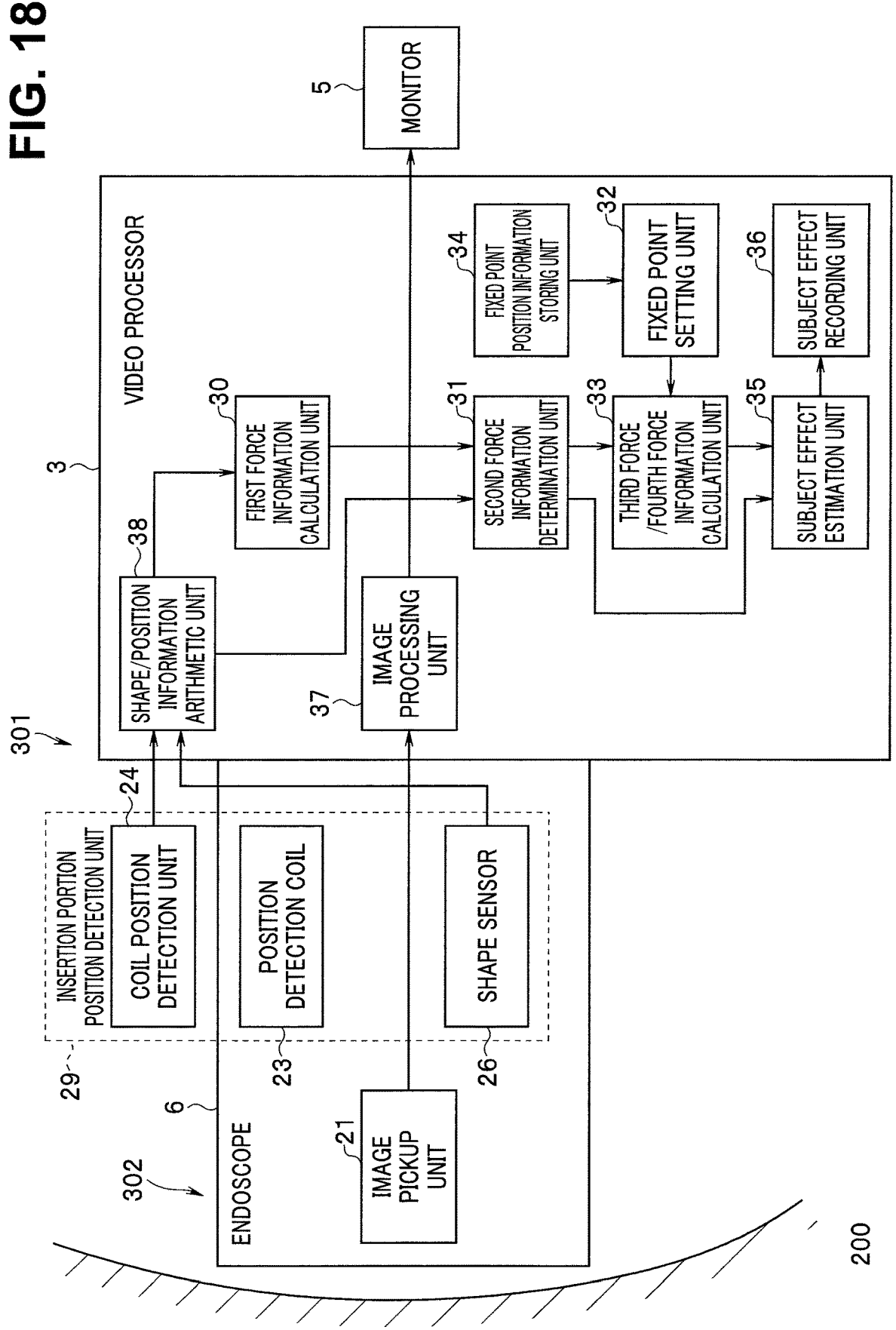
FIG. 18 is a block diagram showing a configuration of an endoscope system of a third embodiment of the present invention.
Figure 19:
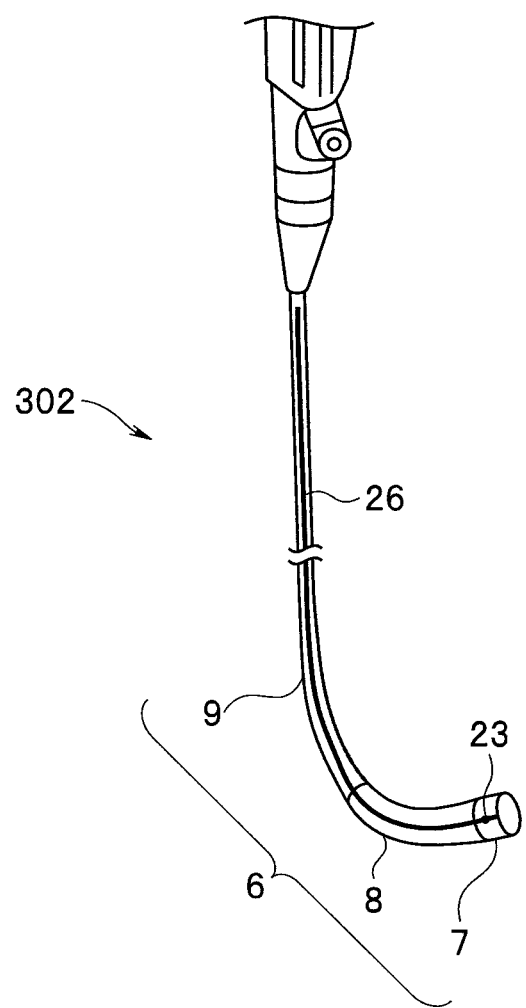
FIG. 19 is an external appearance view of a main part showing a configuration of an insertion portion position detection unit (a magnetic sensor and a shape sensor) of the endoscope system of the third embodiment.

FIG. 18 is a block diagram showing a configuration of an endoscope system of the third embodiment of the present invention. FIG. 19 is an external appearance view of a main part showing a configuration of an insertion portion position detection unit (a magnetic sensor and a shape sensor) of the endoscope system of the third embodiment.

In the above-mentioned endoscope system 1 of the first embodiment, the insertion portion position detection unit 25, which detects the position of the insertion portion 6 inserted into the enteric canal and which outputs a detection signal, is configured of a magnetic sensor including the position detection coils 23 and the coil position detection unit 24. In the endoscope system 101 of the second embodiment, the insertion portion position detection unit is configured of the shape sensor 26, which is provided in the insertion portion 6 of the endoscope 102 and which detects the shape of the insertion portion, and the insertion amount sensor 27, which is provided outside the insertion portion 6 of the endoscope 102 and which detects the insertion length of the insertion portion 6 inserted into the subject 200 during an operation, an inspection or the like.

In contrast, in an endoscope system 301 of the third embodiment, as shown in FIG. 18 and FIG. 19, an insertion portion position detection unit 29 is configured of a magnetic sensor including the shape sensor 26, one position detection coil 23, and the coil position detection unit 24, the shape sensor 26 being provided in the insertion portion 6 of the endoscope 102 to detect the shape of the insertion portion as in the case of the second embodiment, the one position detection coil 23 and the coil position detection unit 24 having functions substantially equivalent to the corresponding functions in the first embodiment.

Other components are substantially equivalent to the corresponding components in the first embodiment and hence, only points which make the third embodiment different from the first embodiment will be described, and the description of the same components will be omitted.

As shown in FIG. 19, an endoscope 302 of the third embodiment includes the shape sensor 26 provided in the insertion portion 6. In the same manner as the above, the shape sensor 26 is a sensor that detects the shape of the insertion portion 6 and, as shown in FIG. 19, is provided inside the whole length of the insertion portion 6. A detection signal relating to the shape of the insertion portion detected by the shape sensor 26 is outputted to the shape/position information arithmetic unit 38 of the video processor 3.

The endoscope 302 also includes the one position detection coil 23 and the coil position detection unit 24. The one position detection coil 23 is provided at the distal end portion 7 of the insertion portion 6, and carries out a function substantially equivalent to the function of the position detection coils 23 of the first embodiment. The coil position detection unit 24 is provided at a position outside the insertion portion 6 to correspond to the position detection coil 23. The one position detection coil 23 and the coil position detection unit 24 form a magnetic sensor substantially equivalent to the magnetic sensor in the first embodiment.

In the third embodiment, the one position detection coil 23 is provided at the distal end portion 7 of the insertion portion 6 as the position detection coil 23 for forming the magnetic sensor. However, the configuration is not limited to the above. A plurality of position detection coils 23 may be provided at the distal end portion 7 or other portions of the insertion portion 6. In other words, it is sufficient for the magnetic sensor of the third embodiment to carry out the function of detecting the position information of the insertion portion 6 in addition to shape information detected by the shape sensor 26. It may be possible to adopt a configuration where, as in the case of the first embodiment, a large number of position detection coils 23 are provided throughout the whole length of the insertion portion 6.

In the third embodiment, the shape/position information arithmetic unit 38 can calculate the position of the insertion portion 6 in the enteric canal based on the information on the shape of the insertion portion 6 obtained by the shape sensor 26, and on the position information of the insertion portion 6 obtained by the magnetic sensor, which is configured of the position detection coil 23 and the coil position detection unit 24.

Other components, operation, and advantageous effects are substantially equivalent to those in the above-mentioned first and second embodiments and hence, the repeated description will be omitted here.

As has been described heretofore, in the same manner as the first embodiment, the endoscope system 301 according to the third embodiment can also provide an endoscope system that estimates information on the state (the magnitude, the direction) of a pressing force applied from the insertion portion 6 to the sigmoid colon or the transverse colon, which is the movable enteric canal which can freely move, and information on the actually pressed position (reaction position) in the enteric canal, and that enables estimation of the effect on the subject at the pressed part (reaction position) based on the information on the state and the information on the actually pressed position.

Fourth Embodiment

Next, a fourth embodiment of the present invention will be described.

Figure 20:
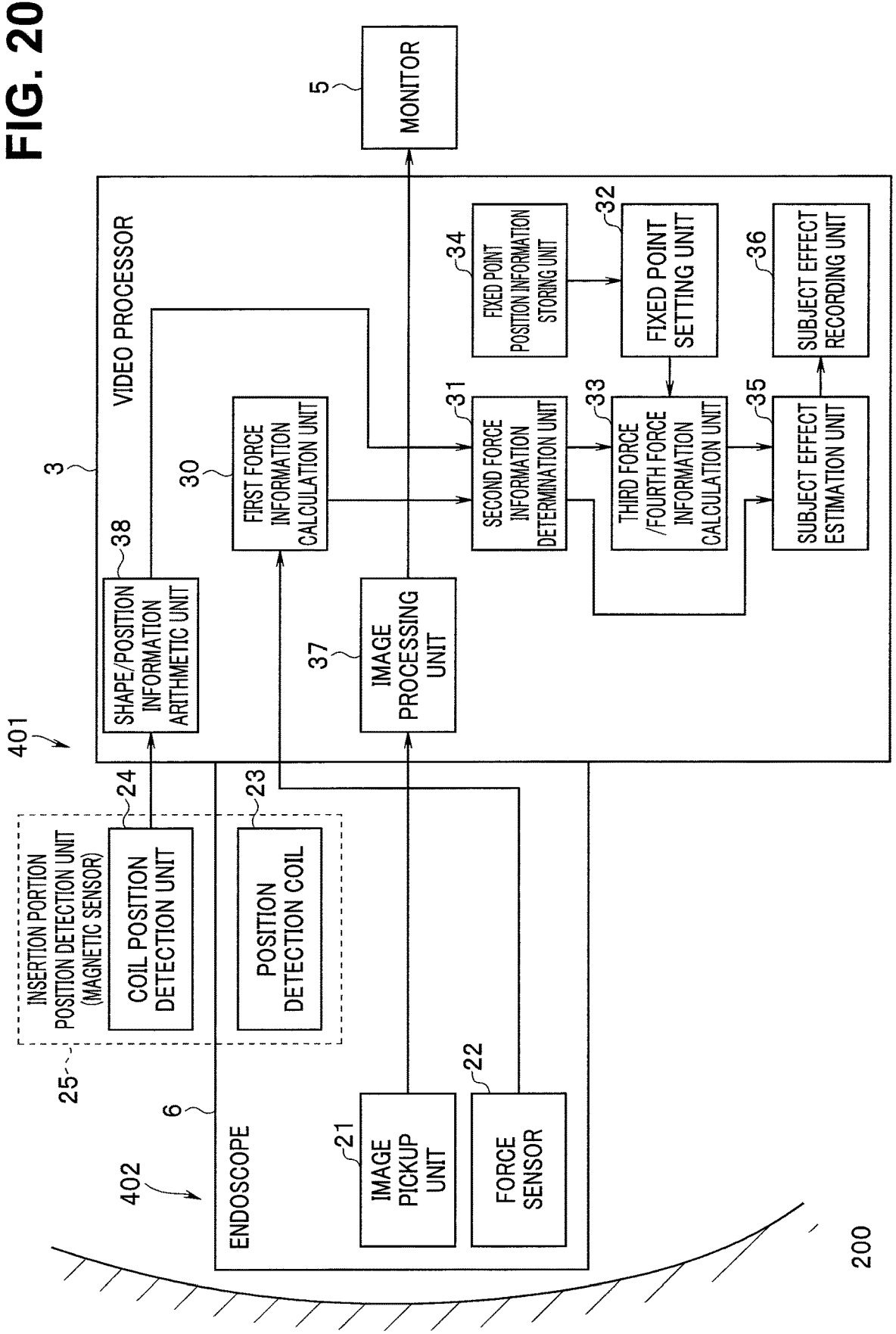
FIG. 20 is a block diagram showing a configuration of an endoscope system according to a fourth embodiment of the present invention.
Figure 21:
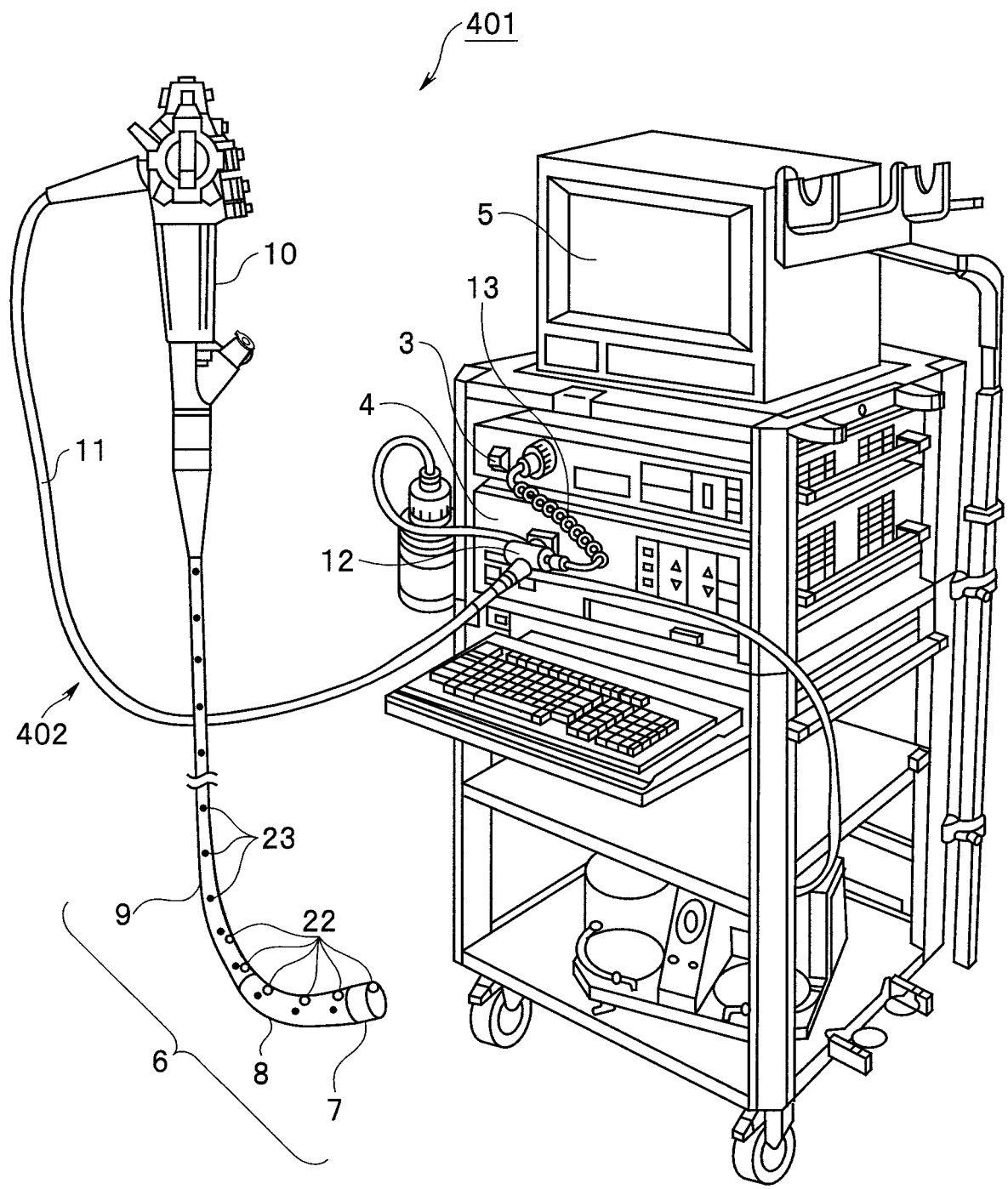
FIG. 21 is an external appearance view showing the configuration of the endoscope system of the fourth embodiment.

FIG. 20 is a block diagram showing a configuration of an endoscope system according to the fourth embodiment of the present invention. FIG. 21 is an external appearance view showing the configuration of the endoscope system of the fourth embodiment.

In the above-mentioned endoscope system 1 of the first embodiment, the first force information calculation unit 30 calculates a pressing force (first force) applied from the enteric canal to the insertion portion 6 based on the shape information and the position information of the insertion portion 6 obtained by the insertion portion position detection unit 25 and the shape/position information arithmetic unit 38.

In contrast, an endoscope system 401 of the fourth embodiment includes the insertion portion position detection unit 25 and the shape/position information arithmetic unit 38, but the first force information calculation unit 30 calculates a pressing force (first force) applied from the enteric canal to the insertion portion 6 based on a detection signal from a force sensor 22 provided in the insertion portion 6 of an endoscope 402 without using shape information and position information of the insertion portion 6 obtained by the shape/position information arithmetic unit 38.

Other components are substantially equivalent to the corresponding components in the first embodiment and hence, only points which make the fourth embodiment different from the first embodiment will be described, and the description of the same components will be omitted.

As shown in FIG. 20 and FIG. 21, in the endoscope 402 of the fourth embodiment, one or a plurality of force sensors 22 configured of a strain gauge, for example, is provided within a range from the distal end portion 7 of the insertion portion 6 to the bending portion 8 and the flexible tube portion 9.

The force sensor 22 is provided on the surface of the insertion portion 6, such as the distal end portion 7, and directly detects a pressing force to the enteric canal when the insertion portion 6 is inserted into the enteric canal of the subject 200. Further, a detection signal of the pressing force is outputted to the first force information calculation unit 30 of the video processor 3.

The force sensor 22 of the fourth embodiment is not limited to the above-mentioned strain gauge, and any of various sensors may be adopted provided that the sensor is a sensor that particularly has a sheet shape, and that can be attached to the surface of the insertion portion 6, such as a pressure sensor.

In the fourth embodiment, the force sensor 22 is disposed at the main part on the surface of the insertion portion within the range from the distal end portion 7 of the insertion portion 6 to the bending portion 8 and the flexible tube portion 9. However, needless to say, the position where the force sensor 22 is disposed may be suitably set depending on the type of the endoscope 402 for the large intestine.

In the fourth embodiment, the first force information calculation unit 30 is configured to calculate a pressing force (first force) applied from the enteric canal to the insertion portion 6 based on only a detection signal from the force sensor 22 without using shape information and position information of the insertion portion 6 obtained by the shape/position information arithmetic unit 38 as described above.

However, when necessary, shape information and position information of the insertion portion 6 obtained by the shape/position information arithmetic unit 38 may also be used.

As has been described heretofore, the endoscope system 401 according to the fourth embodiment can directly detect a contact with the enteric canal and hence, it is possible to more accurately detect a pressing force which the insertion portion 6 receives from the enteric canal and the reaction force of the pressing force.

In the above-mentioned embodiment, all of the shape/position information arithmetic unit 38, the first force information calculation unit 30, the second force information determination unit 31, the third force/fourth force information calculation unit 33, the fixed point setting unit 32, the subject effect estimation unit 35, and the subject effect recording unit 36 are provided in the video processor 3 connected to the endoscope. However, the configuration is not limited to the above.

In other words, some or all of the above-mentioned respective constitutional elements may be provided in an external device of the video processor 3. An example of the external device may be the endoscope, such as the connector portion 12 of the endoscope (see FIG. 2).

Further, the above-mentioned shape/position information arithmetic unit 38 and/or the first force information calculation unit 30 may be integrally configured with the insertion portion position detection unit 25 provided in the endoscope 2 (first and fourth embodiments), the insertion portion position detection unit 28 (second embodiment), or the insertion portion position detection unit 29 (third embodiment). The control device may include the insertion portion position detection unit 25, 28, or 29.

The present invention is not limited to the above-mentioned embodiments, and various modifications and applications are conceivable without departing from the gist of the present invention.

What is claimed is:

1. An endoscope system comprising:
an insertion portion comprising a distal end and a proximal end, and configured to:
be inserted into an enteric canal of a subject from a side of the distal end of the insertion portion and come into contact with an inner wall of the enteric canal, to thereby receive a first force from the enteric canal; and
apply a second force as a reaction force of the first force to the enteric canal, the insertion portion having flexibility;

an insertion portion position detection device configured to detect a relative position of the insertion portion, inserted into the enteric canal, with respect to the enteric canal, and to output a detection signal; and a processor configured to:
  calculate first force information including a position of a point of application of the first force in the insertion portion, a direction of the first force, and a magnitude of the first force;
  perform an arithmetic operation of shape information and position information of the insertion portion in the enteric canal based on the detection signal relating to a position of the insertion portion detected by the insertion portion position detection device;
  determine second force information including a reaction position, the reaction position being a position at which the enteric canal receives the second force, based on the position information of the insertion portion in the enteric canal obtained by the arithmetic operation, and on the position information, which is calculated, of the point of application of the first force in the insertion portion;
  set position information of a first fixed point and a second fixed point as a calculation condition, the first fixed point and the second fixed point being portions of the enteric canal that are partially fixed from outside the enteric canal; and
  calculate, based on the calculation condition which is set, third force/fourth force information such that a resultant force of a third force directed toward the first fixed point from the reaction position and a fourth force directed toward the second fixed point from the reaction position is balanced with the second force, the third force/fourth force information including a magnitude and a direction of the third force, and a magnitude and a direction of the fourth force.

2. The endoscope system according to claim 1, further comprising a memory configured to store in advance position information of the first fixed point and position information of the second fixed point,
  wherein the processor is configured to set, as the calculation condition, the position information of the first fixed point and the position information of the second fixed point stored in the memory.

3. The endoscope system according to claim 1,
  wherein the insertion portion position detection device comprises a magnetic sensor comprising:
    a plurality of coils provided in the insertion portion and configured to transmit or receive a magnetic field; and
    a coil position detector configured to receive or transmit the magnetic field, and identify positions of the plurality of coils with respect to the coil position detector, thus detecting the relative position of the insertion portion with respect to the enteric canal in a state where the insertion portion is inserted into the enteric canal of the subject.

4. The endoscope system according to claim 3,
  wherein the processor is configured to calculate the first force information based on an output from the insertion portion position detection device comprising the magnetic sensor.

5. The endoscope system according to claim 1,
  wherein the insertion portion position detection device comprises a shape sensor and an insertion amount sensor, the shape sensor being provided in the insertion portion, and being configured to detect a shape of the insertion portion, the insertion amount sensor being configured to detect an amount of insertion of the insertion portion into the subject.

6. The endoscope system according to claim 5,
  wherein the processor is configured to calculate the first force information based on the shape from the shape sensor and the amount of insertion from the insertion amount sensor.

7. The endoscope system according to claim 1, further comprising a force sensor provided in the insertion portion, and configured to detect a force applied to the insertion portion,
  wherein the processor is configured to calculate the first force information according to an output from the force sensor.

8. The endoscope system according to claim 1,
  wherein the first fixed point is a predetermined point in an enteric canal fixed portion where an upper rectum, a lower rectum, or an anal canal is fixed, and
  wherein the processor is configured to:
    infer a position of the first fixed point based on the position of the insertion portion detected by the insertion portion position detection device; and
    set the position of the first fixed point inferred as the calculation condition.

9. A control device connected to an endoscope including an insertion portion having a distal end and a proximal end, and configured to be inserted into an enteric canal of a subject from a side of the distal end of the insertion portion and come into contact with an inner wall of the enteric canal, to thereby receive a first force from the enteric canal, and apply a second force as a reaction force of the first force to the enteric canal, the insertion portion having flexibility, the control device comprising:
  an insertion portion position detection device configured to detect a relative position of the insertion portion, inserted into the enteric canal, with respect to the enteric canal, and to output a detection signal; and
  a processor configured to:
    calculate first force information including a position of a point of application of the first force in the insertion portion, a direction of the first force, and a magnitude of the first force;
    perform an arithmetic operation of shape information and position information of the insertion portion in the enteric canal based on the detection signal relating to a position of the insertion portion detected by the insertion portion position detection device;
    determine second force information including a reaction position, the reaction position being a position at which the enteric canal receives the second force, based on the position information of the insertion portion in the enteric canal obtained by the arithmetic operation, and on the position information, which is calculated, of the point of application of the first force in the insertion portion;
    set position information of a first fixed point and a second fixed point as a calculation condition, the first fixed point and the second fixed point being portions of the enteric canal that are partially fixed from outside the enteric canal; and
    calculate, based on the calculation condition which is set, third force/fourth force information such that a resultant force of a third force directed toward the first fixed point from the reaction position and a fourth force directed toward the second fixed point from the reaction position is balanced with the second force, the third force/fourth force information including a magnitude and a direction of the third force, and a magnitude and a direction of the fourth force.

* * * * *